(12) United States Patent
Le Bourdonnec et al.

(10) Patent No.: US 8,288,546 B2
(45) Date of Patent: *Oct. 16, 2012

(54) SUBSTITUTED PIPERIDINE COMPOUNDS AND METHODS OF THEIR USE

(75) Inventors: Bertrand Le Bourdonnec, East Fallowfield, PA (US); Roland E. Dolle, King of Prussia, PA (US)

(73) Assignee: Adolor Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/897,824

(22) Filed: Oct. 5, 2010

(65) Prior Publication Data

US 2011/0034417 A1 Feb. 10, 2011

Related U.S. Application Data

(62) Division of application No. 11/217,528, filed on Sep. 1, 2005, now Pat. No. 7,820,827, which is a division of application No. 10/462,507, filed on Jun. 16, 2003, now Pat. No. 6,992,090.

(51) Int. Cl.
C07F 9/28 (2006.01)
(52) U.S. Cl. .......................................... 546/22
(58) Field of Classification Search .................. 546/22
See application file for complete search history.

(56) References Cited

U.S. PATENT DOCUMENTS

| | | | |
|---|---|---|---|
| 4,191,771 A | 3/1980 | Zimmerman | |
| 4,236,010 A | 11/1980 | Imhof et al. | |
| 4,931,558 A | 6/1990 | Barnett | |
| 6,451,806 B2 * | 9/2002 | Farrar | 514/282 |
| 6,531,481 B2 | 3/2003 | Carroll et al. | |
| 6,552,032 B2 | 4/2003 | Carroll et al. | |
| 6,593,348 B2 | 7/2003 | Carroll et al. | |
| 6,812,236 B2 | 11/2004 | Gibson et al. | |
| 6,900,228 B1 | 5/2005 | Carroll et al. | |
| 6,992,090 B2 * | 1/2006 | Le Bourdonnec et al. | 514/317 |
| 7,381,721 B2 | 6/2008 | Dolle et al. | |
| 7,820,827 B2 | 10/2010 | Le Bourdonnec et al. | |
| 2003/0100562 A1 | 5/2003 | Cheng et al. | |
| 2004/0204453 A1 | 10/2004 | McHardy et al. | |
| 2005/0032837 A1 | 2/2005 | McHardy et al. | |

FOREIGN PATENT DOCUMENTS

| | | |
|---|---|---|
| EP | 1072592 | 1/2001 |
| EP | 1359146 | 5/2003 |
| WO | WO 99/45925 | 9/1999 |
| WO | WO 02/053533 | 7/2002 |

OTHER PUBLICATIONS

Sigma-Aldrich online catalog of Wang Resins (2011).*
Barratt S. McG. et al., "Approaches to Reducing Postoperative Opioid Requirements," CNS Drugs, Disease Management, Oct. 1998, 10 (4), 257-270.
Barratt S., McG., "Advances in Acute Pain Management," Int. Anesthesiol. Clin. 1997 Spring; 35(2):27-47.
Gastroenterology, A730 AGA Abstracts, 114(4), Apr. 15, 1998.
LY246736 Dihydrate, Opioid Receptor Antagonist, Drugs of the Future, 1994, 19(12), 1078-1083.
Werner, John A., et al., "Synthesis of *trans*-3, 4-Dimethyl-4-(3-hydroxyphenyl) piperidine Opioid Antagonists: Application of the *Cis*-Thermal Elimination of Carbonates to Alkaloid Synthesis," J. Org. Chem., 1996, 61(2), 587-597.
Statnick M.A., et al., "Antagonism of opioid receptors reduces body fat in obese rats by decreasing food intake and stimulating lipid utilization," American Journal of Physiology—Regulatory, Integrative and Comparative Physiology, 2003, 284: R1399-R1408.

* cited by examiner

*Primary Examiner* — Janet Andres
*Assistant Examiner* — John Mabry
(74) *Attorney, Agent, or Firm* — Feldman Gale, P.A.; Walter C. Frank

(57) ABSTRACT

Novel 3,4-disubstituted-4-aryl-piperidine compounds are disclosed. Pharmaceutical compositions containing the 3,4-disubstituted-4-aryl-piperidine compounds and methods of their pharmaceutical uses are also disclosed. The compounds disclosed are useful, inter alia, as antagonists of opioid receptors.

17 Claims, No Drawings

SUBSTITUTED PIPERIDINE COMPOUNDS AND METHODS OF THEIR USE

CROSS REFERENCE TO RELATED APPLICATIONS

This application is a Divisional of Application No. 11/217,528, filed Sep. 1, 2005, which is now U.S. Pat. No. 7,820,827, which is a Divisional of application Ser. No. 10/462,507, filed Jun. 16, 2003 which is now U.S. Pat. No. 6,992,090, the entirety of each of which is hereby incorporated herein by reference.

FIELD OF THE INVENTION

The present invention relates to compounds that affect the opioid receptor system and, more particularly, to 3,4-disubstituted-4-aryl-piperidine compounds and pharmaceutical compositions containing such compounds that are, inter alia, antagonists of opioid receptors.

BACKGROUND OF THE INVENTION

It is well known that opioid drugs target three types of endogenous opioid receptors (i.e., $\mu$, $\delta$, and $\kappa$ receptors) in biological systems. Many opiates, such as morphine, are $\mu$ opioid agonists that are often used as analgesics for the treatment of severe pain due to their activation of $\mu$ opioid receptors in the brain and central nervous system (CNS). Opioid receptors are, however, not limited to the CNS, and may be found in other tissues throughout the body, i.e., peripheral to the CNS. A number of side effects of opioid drugs may be caused by activation of these peripheral receptors. For example, administration of $\mu$ opioid agonists often results in intestinal dysfunction due to the large number of receptors in the wall of the gut (Wittert, G., Hope, P. and Pyle, D., *Biochemical and Biophysical Research Communications*, 1996, 218, 877-881; Bagnol, D., Mansour, A., Akil, A. and Watson, S. J., *Neuroscience*, 1997, 81, 579-591). Specifically, opioids are generally known to cause nausea and vomiting, as well as inhibition of normal propulsive gastrointestinal function in animals and man (Reisine, T., and Pasternak, G., *Goodman & Gilman's The Pharmacological Basis of Therapeutics, Ninth Edition*, 1996, 521-555), resulting in side effects such as, for example, constipation.

Recent evidence has indicated that naturally-occurring endogenous opioid compounds may also affect propulsive activity in the gastrointestinal (GI) tract. Met-enkephalin, which activates $\mu$ and $\delta$ receptors in both the brain and gut, is one of several neuropeptides found in the GI tract (Koch, T. R., Carney, J. A., Go, V. L., and Szurszewski, J. H., *Digestive Diseases and Sciences*, 1991, 36, 712-728). Additionally, receptor knockout techniques have shown that mice lacking µ opioid receptors may have faster GI transit times than wild-type mice, suggesting that endogenous opioid peptides may tonically inhibit GI transit in normal mice (Schuller, A. G. P., King, M., Sherwood, A. C., Pintar, J. E., and Pasternak, G. W., *Society of Neuroscience Abstracts* 1998, 24, 524). Studies have shown that opioid peptides and receptors located throughout the GI tract may be involved in normal regulation of intestinal motility and mucosal transport of fluids in both animals and man (Reisine, T., and Pasternak, G., Goodman & Gilman's *The Pharmacological Basis of Therapeutics, Ninth Edition*, 1996, 521-555). Other studies show that the sympathetic nervous system may be associated with endogenous opioids and control of intestinal motility (Bagnol, D., Herbrecht, F., Jule, Y., Jarry, T., and Cupo, A., *Regul. Pept.*, 1993, 47, 259-273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or post-operative) ileus. "Ileus," as used herein, refers to the obstruction of the bowel or gut, especially the colon. See, e.g., *Dorland's Illustrated Medical Dictionary*, 27th ed., page 816, (W.B. Saunders Company, Philadelphia, Pa., 1988). Ileus should be distinguished from constipation, which refers to infrequency of or difficulty in feces evacuation. See, e.g., *Dorland's Illustrated Medical Dictionary*, 27th ed., page 375, (W. B. Saunders Company, Philadelphia, 1988). Ileus may be diagnosed by the disruption of normal coordinated movements of the gut, resulting in failure of intestinal contents propulsion. See, e.g., Resnick, J., Am. *J. of Gastroenterology*, 1997, 92, 751 and Resnick, J., Am. *J. of Gastroenterology*, 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, Jr., E. D., *Digestive Diseases and Sciences*, 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics, for pain relief after surgery, particularly major surgery, current post-surgical pain treatment may actually slow recovery of normal bowel function, resulting in a delay in hospital discharge and increasing the cost of medical care.

Post-surgical and post-partum ileus may also occur in the absence of exogenous opioid agonists. It would be of benefit to inhibit the natural activity of endogenous opioids during and/or after periods of biological stress, such as surgery and childbirth, so that ileus and related forms of bowel dysfunction can be prevented and/or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased, in addition to the benefit of minimizing patient discomfort. Thus, drugs that selectively act on opioid receptors in the gut would be ideal candidates for preventing and/or treating post-surgical and post-partum ileus. Of those, drugs that do not interfere with the effects of opioid analgesics in the CNS would be of special benefit in that they could be administered simultaneously for pain management with limited side effects.

Peripheral opioid antagonists that do not cross the blood-brain barrier into the CNS are known in the literature and have been tested in relation to their activity on the GI tract. In U.S. Pat. Nos. 5,250,542, 5,434,171, 5,159,081, and 5,270,328, peripherally selective piperidine-N-alkylcarboxylate opioid antagonists are described as being useful in the treatment of idiopathic constipation, irritable bowel syndrome, and opioid-induced constipation. In addition, U.S. Pat. No. 4,176,186 describes quaternary derivatives of noroxymorphone (i.e., methylnaltrexone) that are said to prevent or relieve the intestinal immobility side effect of narcotic analgesics without reducing analgesic effectiveness. U.S. Pat. No. 5,972,954 describes the use of methylnaltrexone, enteric-coated methylnaltrexone, or other quaternary derivatives of noroxymorphone for preventing and/or treating opioid- and/or nonopioid-induced side effects associated with opioid administration.

General opioid antagonists, such as naloxone and naltrexone, have also been implicated as being useful in the treatment of GI tract dysmotility. For example, U.S. Pat. No. 4,987,126 and Kreek, M. J. Schaefer, R. A., Hahn, E. F., Fishman, *J. Lancet*, 1983, 1, 8319, 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G., *Am. J. Gastroenerol.*, 1985, 80, 6, 407). Furthermore, it has been implicated that naloxone may provide therapy for paralytic ileus (Mack, D. J. Fulton, J. D., *Br. J. Surg.*, 1989, 76, 10, 1101). However, it is well known that activity of naloxone and 7 related drugs is not limited to peripheral systems and may interfere with the analgesic effects of opioid narcotics.

Inasmuch as post-surgical and post-partum ileus, for example, are common illnesses that add to the cost of health care and as yet have no specific treatments, there is a need for a specific and effective remedy. The majority of currently known opioid antagonist therapies is not peripherally selective and has the potential for undesirable side effects resulting from penetration into the CNS. Given the estimated 21 million inpatient surgeries and 26 million outpatient surgeries each year, and an estimate of 4.7 million patients experiencing post-surgical ileus, methods involving opioid antagonists that are not only specific for peripheral systems, but also specific for the gut, are desirable for treating post-surgical and post-partum ileus.

There is still an unfulfilled need for compounds that may be used in methods to antagonize opioid receptors, particularly where undesirable symptoms or conditions are side effects of administering exogenous opioids. The present invention is directed to these, as well as other important ends.

SUMMARY OF THE INVENTION

Accordingly, the present invention is directed, in part, to novel pharmaceutically active compounds of formula I:

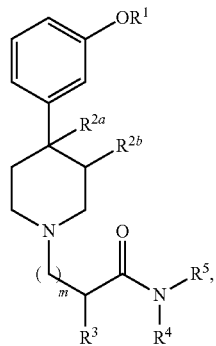

I wherein:
$R^1$ is H or alkyl;
$R^{2a}$ is alkyl or alkenyl;
$R^{2b}$ is H, alkyl, or alkenyl;
$R^3$ is H, alkyl, alkenyl, aryl, cycloalkyl, cycloalkenyl, cycloalkylalkyl, cycloalkenylalkyl, or aralkyl;
$R^4$ is:
  H,
  aryl (optionally substituted by one or more substituents selected from —OH, nitro, halo, —CN, —CH$_2$CN, —C(=O)NH$_2$, —CO$_2$H, —N($R^{6a}$)($R^{6b}$), alkoxycarbonyl, aryloxy, aryl, alkyl, alkoxy, and alkanoyl (which latter three groups are optionally substituted by one or more halo atoms)),
  aralkyl;
  alkyl,
  alkenyl or
  alkynyl,
  which latter three groups are optionally substituted by one or more substituents selected from —$OR^{6c}$, —S(=O)$_q R^{6d}$, —CN, halo, alkoxycarbonyl, —N($R^{6a}$)($R^{6b}$), alkanoyl, alkanoyloxy, cycloalkyl, cycloalkanoyl, —N($R^{6e}$)S(=O)$_2 R^{7a}$, —P(=O)$OR^{7b}OR^{7c}$, Het$^1$, and aryl (which latter group is optionally substituted by one or more substituents selected from —OH, nitro, —N($R^{6a}$)($R^{6b}$), halo, —CN, —CH$_2$CN, —C(=O)NH$_2$, —CO$_2$H, —CHO, aryl, alkyl, alkoxy, aralkoxy, aryloxy, and alkanoyl (which latter three groups are optionally substituted by one or more halo atoms));
$R^{6a}$, $R^{6b}$, $R^{6c}$, $R^{6d}$, and $R^{6e}$, are each independently H, Het$^2$, alkyl, alkenyl, alkynyl, cycloalkyl, aralkyl, or aryl (which latter six groups are optionally substituted by one or more substituents selected from OH, nitro, halo, —NHC(=O)$R^3$, —CN, —CH$_2$CN, —C(=O)NH$_2$, —CO$_2$H, alkoxycarbonyl, alkyl, alkoxy, and alkanoyl (which latter three groups are optionally substituted by one or more halo atoms));
$R^5$ is —(CH$_2$)$_y$(CHR$^8$)$_j$(CHR$^{8a}$)$_z$W, —CH$_2$P(=O)$OR^{7b}OR^{7c}$, or —S(=O)$_2 R^{7d}$;
$R^8$ is each independently aryl (optionally substituted by one or more substituents selected from —OH, nitro, aryl, halo, —CN, —CH$_2$CN, —C(=O)NH$_2$, —CO$_2$H, —N($R^{6a}$)($R^{6b}$), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —$OR^{6c}$, —S(O)$_q R^{6d}$, —CN, halo, —N($R^{6a}$)($R^{6b}$), —CO$_2$H, —C(=O)NH$_2$, alkoxycarbonyl, alkanoyl, alkanoyloxy, cycloalkyl, cycloalkanoyl, —N($R^{6e}$)S(=O)$_2 R^{7a}$, —P(=O)$OR^{7b}OR^{7c}$, Het$^1$, and aryl (which latter group is optionally substituted by one or more substituents selected from —OH, nitro, amino, halo, —CN, —CH$_2$CN, —C(=O)NH$_2$, —CO$_2$H, aroyl, aryl, alkyl, alkoxy, and alkanoyl (which latter three groups are optionally substituted by one or more halo atoms)); or $R^4$ and $R^8$ when taken together with the atoms through which they are connected, form a 4- to 8-membered heterocycloalkyl ring, wherein said heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy;

and wherein the heterocycloalkyl ring is also optionally interrupted by one or more O, S or N($R^{11}$) groups;

$R^{8a}$ is each independently H, aryl (optionally substituted by one or more substituents selected from —OH, nitro, aryl, halo, —CN, —$CH_2CN$, —C(=O)$NH_2$, —$CO_2H$, —N($R^{6a}$)($R^{6b}$), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —$OR^{6c}$, —S(O)$_q R^{6d}$, —CN, halo, amino, —$CO_2H$, —C(=O)$NH_2$, alkoxycarbonyl, alkanoyl, alkanoyloxy, cycloalkyl, cycloalkanoyl, —N($R^{6e}$)S(=O)$_2 R^{7a}$, —P(=O)$OR^{7b}OR^{7c}$, $Het^1$, and aryl (which latter group is optionally substituted by one or more substituents selected from —OH, nitro, amino, halo, —CN, —$CH_2CN$, —C(=O)$NH_2$, —$CO_2H$, aroyl, aryl, alkyl, alkoxy, and alkanoyl (which latter three groups are optionally substituted by one or more halo atoms)); or $R^4$ and $R^{8a}$ when taken together with the atoms through which they are connected, form a 4- to 8-membered heterocycloalkyl ring, wherein said heterocycloalkyl ring is optionally fused to an aromatic ring, and wherein said heterocycloalkyl ring, or the aromatic ring to which is optionally fused, is each independently optionally substituted by one or more substituents selected from —OH, alkyl, or alkoxy; and wherein the heterocycloalkyl ring is also optionally interrupted by one or more O, S or N($R^{11}$) groups;

W is —C(=O)$OR^9$, —C(=O)N($R^{10a}$)$R^{10b}$), or —P(=O)$OR^{7b}OR^{7c}$;

$R^9$ is H, alkyl, alkenyl, phenyl, cycloalkyl, cycloalkenyl, cycloalkylalkyl, cycloalkenylalkyl, or aralkyl;

$R^{10a}$ and $R^{10b}$, each independently represent H, alkyl, alkenyl, alkynyl, cycloalkyl, aralkyl, $Het^3$, or aryl (which latter seven groups are optionally substituted by one or more substituents selected from —OH, nitro, halo, —CN, —$CH_2CN$, —C(=O)$NH_2$, —$CO_2H$, alkyl, alkoxy, and alkanoyl (which latter three groups are optionally substituted by one or more halo atoms)); or $R^{10a}$ and $R^{10b}$ when taken together with the nitrogen atom to which they are attached form a 4- to 8-membered heterocycloalkyl ring, wherein said heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N($R^{12}$) groups;

$R^{7a}$, $R^{7b}$, $R^{7c}$, and $R^{7d}$, are each independently H, alkyl, cycloalkyl, alkaryl, aralkyl or aryl, which latter five groups are optionally substituted by one or more substituents selected from alkyl, alkoxy, —OH, nitro, amino and halo;

$Het^1$, $Het^2$ and $Het^3$ each independently represent a 3- to 8-membered heterocyclic ring, wherein said heterocyclic ring contains at least one heteroatom selected from oxygen, sulfur, nitrogen or combinations thereof, wherein said heterocyclic ring is optionally fused to an aromatic ring, and wherein said heterocyclic ring, or the aromatic ring to which it is optionally fused, is each independently optionally substituted by one or more substituents selected from —OH, =O, nitro, amino, halo, —CN, —$CO_2H$, aryl, alkyl, alkoxy and alkanoyl (which latter three groups are optionally substituted by one or more halo atoms);

$R^{11}$ represents H, alkyl, cycloalkyl, cycloalkylalkyl, or aralkyl;

$R^{12}$ represents H, alkyl, cycloalkyl, cycloalkylalkyl, or aralkyl;

j is the integer 0, 1, 2, 3, or 4;
m is the integer 0, 1, 2, 3, or 4;
q is the integer 0, 1, or 2;
y is the integer 0, 1, 2, 3, 4, or 5; and
z is the integer 0, 1, 2, 3, or 4;
with the proviso that when j and z are each the integer 0, y must be the integer 5;

or a stereoisomer, prodrug, pharmaceutically acceptable salt, hydrate, solvate, acid hydrate, N-oxide or isomorphic crystalline form thereof.

In another embodiment, the invention is directed to pharmaceutical compositions comprising a pharmaceutically acceptable carrier and an effective amount of a compound of formula I.

In yet another embodiment, the invention is directed to methods for binding opioid receptors, in a patient in need thereof, comprising the step of: administering to said patient an effective amount of a compound of formula I.

In other embodiments, the invention is directed to methods for binding opioid receptors, comprising the step of:

administering to said patient an effective amount of a compound of formula I;

where the 3,4-disubstituted-4-aryl-piperidine compound exhibits activity toward the opioid receptors (selected from μ, κ, or combinations thereof).

In some preferred embodiments, the invention is directed to methods where the patient is in need of prevention or treatment of a condition, disease or undesirable side effect caused by an endogenous or exogenous opioid.

In a particularly preferred embodiment, the invention is directed to methods for preventing or treating gastrointestinal dysfunction.

In yet another preferred embodiment, the invention is directed to methods of preventing or treating pain, comprising the step of:

administering to a patient in need thereof, a composition, comprising an effective amount of an opioid; and an effective amount of a compound of formula I.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, or branched, hydrocarbon having from about 1 to about 10 carbon atoms (and all combinations and subcombinations of ranges and specific numbers of carbon atoms therein). In some embodiments, it is preferred that the alkyl groups have from about 1 to about 4 carbon atoms. In others, it is preferred that the alkyl groups have from about 1 to about 5 carbon atoms. In still others, it is preferred that the alkyl groups have from about 1 to about 6 carbon atoms. Alkyl groups can be optionally substituted. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkenyl" refers to an alkyl group having from about 2 to about 10 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups can be optionally substituted.

As used herein, "alkynyl" refers to an alkyl group having from about 2 to about 10 carbon atoms and one or more triple bonds (and all combinations and subcombinations of ranges and specific numbers of carbon atoms therein), wherein alkyl is as previously defined. Alkynyl groups can be optionally substituted.

As used herein, "aryl" and "aromatic" each refer to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Exemplary aryl groups include, but are not limited to, phenyl, naphthyl, anthracenyl, and phenanthrenyl.

As used herein, "aralkyl" refers to alkyl radicals bearing one or more aryl substituents and having from about 6 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups can be optionally substituted. Exemplary aralkyl groups include, but are not limited to, benzyl, diphenylmethyl, triphenylmethyl, phenylethyl, and diphenylethyl.

As used herein, "alkaryl" refers to an optionally substituted, mono-, di-, tri-, or other multicyclic aryl radical bearing one or more alkyl substituents and having from about 5 to about 50 carbon atoms (and all combinations and subcombinations of ranges and specific numbers of carbon atoms therein), and wherein aryl and alkyl are as previously defined. In some preferred embodiments, the alkyl substituents of the alkaryl groups have from about 1 to about 4 carbon atoms. Alkaryl groups can be optionally substituted. Exemplary alkaryl groups include, but are not limited to, tolyl, xylyl, 1-methylnaphthyl, 9-ethylanthracenyl, and 2,4-dimethylphenanthrenyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Exemplary heteroaryl groups include, but are not limited to, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structure and having from about 3 to about 20 carbon atoms (and all combinations and subcombinations of ranges and specific numbers of carbon atoms therein). In some preferred embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1] heptanyl], and 2-[1,2,3,4-tetrahydro-naphthalenyl].

As used herein, "cycloalkenyl" refers to an optionally substituted, alkyl group having one or more rings in their structure, wherein the ring is partially unsaturated, that is, having one or more double bonds within the ring, and having from about 3 to about 20 carbon atoms (and all combinations and subcombinations of ranges and specific numbers of carbon atoms therein). In some preferred embodiments, the cycloalkenyl groups have from about 5 to about 8 carbon atoms. Multi-ring structures may be bridged or fused ring structures, wherein the additional groups fused or bridged to the cycloalkenyl ring may include optionally substituted cycloalkyl, aryl, heterocycloalkyl, or heteroaryl rings. Exemplary cycloalkenyl groups include, but are not limited to, cyclopropenyl, cyclobutenyl, cyclopentenyl, cyclohexenyl, cyclooctenyl, bicyclo[2.2.1]hept-5-en-2-yl, bornenyl, [2.2.2]-bicyclooct-5-en-2-yl, octahydronaphthalenyl, beta-pinenyl, camphenyl, fenchenyl, α-pinenyl, and dicyclopentadienyl.

As used herein, "alkylcycloalkyl" refers to an optionally substituted ring system comprising a cycloalkyl radical having one or more alkyl substituents, wherein cycloalkyl and alkyl are as previously defined. Exemplary alkylcycloalkyl groups include, but are not limited to, 2-methylcyclohexyl, 3,3-dimethylcyclopentyl, trans-2,3-dimethylcyclooctyl, and 4-methyldecahydronaphthalenyl.

As used herein, "cycloalkylalkyl" refers to an optionally substituted alkyl radical having one or more cycloalkyl substituents, wherein cycloalkyl and alkyl are as previously defined. In some preferred embodiments, the alkyl moieties of the cycloalkylalkyl groups have from about 1 to about 3 carbon atoms. Exemplary cycloalkylalkyl groups include, but are not limited to, cyclohexylmethyl, 4-[4-methyldecahydronaphthalenyl]-pentyl, 3-[trans-2,3-dimethylcyclooctyl]-propyl, and cyclopentylethyl.

As used herein, "cycloalkenylalkyl" refers to an optionally substituted alkyl radical having one or more cycloalkenyl substituents, wherein cycloalkenyl and alkyl are as previously defined. In some preferred embodiments, the alkyl moieties of the cycloalkenylalkyl groups have from about 1 to about 3 carbon atoms. Exemplary cycloalkenylalkyl groups include, but are not limited to, 4-[4-methyloctahydronaphthalenyl]-pentyl, cyclohexenylmethyl, 3-[trans-2,3-dimethylcyclooctenyl]-propyl, and cyclopentenylethyl.

As used herein, "heteroaralkyl" refers to optionally substituted alkyl radicals having one or more heteroaryl substituents and the heteroaralkyl groups having from about 2 to about 50 carbon atoms (and all combinations and subcombinations of ranges and specific numbers of carbon atoms therein), wherein heteroaryl and alkyl are as previously defined. In some preferred embodiments, the heteroaralkyl groups have from about 6 to about 25 carbon atoms. Non-limiting examples include, but are not limited to, 5-(2H-tetrazolyl)methyl, 2-(1H-pyrrol-3-yl)ethyl, 3-pyridylmethyl, and 3-(pyrimidin-2-yl)-2-methylcyclopentanyl.

As used herein, "heterocyclic" refers to an optionally substituted heteroaryl or heterocycloalkyl ring, wherein heteroaryl and heterocycloalkyl are as previously defined. In some preferred embodiments, the heterocyclic groups have from about 3 to about 8 carbon atoms.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein). In some preferred embodiments the heterocyclic groups have from about 4 to about 8 carbons. In other embodiments the heterocycloalkyl group may be unsaturated, that is to say, they have one or more double bonds. In still other embodiments, the heterocyclic groups may be fused to aromatic rings. Exemplary heterocycloalkyl groups include, but are not limited to, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydrocyclopenta[c]pyranyl, 1,2,3,4,-tetrahydro quinolyl, octahydro-[2]pyrindinyl, decahydro-cycloocta[c]furanyl, tetrahydroquinolyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7] dodecane.

As used herein, the term "alkoxy" refers to an optionally substituted alkyl-O-group wherein alkyl is as previously defined. In some preferred embodiments the alkyl moieties of the alkoxy groups have from about 1 to about 4 carbon atoms. Exemplary alkoxy groups include, but are not limited to, methoxy, ethoxy, n-propoxy, i-propoxy, n-butoxy, and heptoxy.

As used herein, the term "aryloxy" refers to an optionally substituted aryl-O-group wherein aryl is as previously defined. Exemplary aryloxy groups include, but are not limited to, phenoxy and naphthoxy.

As used herein, the term "aralkoxy" refers to an optionally substituted aralkyl-O-group wherein aralkyl is as previously defined. Exemplary aralkoxy groups include, but are not limited to, benzyloxy, 1-phenylethoxy, 2-phenylethoxy, and 3-naphthylheptoxy.

As used herein, the term "aroyl" refers to a carbonyl —C(=O)— group with an aryl moieties wherein aryl is as previously defined. The aryl moieties of aroyl groups can be optionally substituted. Exemplary aroyl groups include, but are not limited to, benzoyl and para-methoxybenzoyl.

As used herein, "carboxy" refers to a —C(=O)OH group.

As used herein, "alkanoyl" refers to a —C(=O)-alkyl group, wherein alkyl is as previously defined. In some preferred embodiments the alkyl moieties of the alkanoyl groups have from about 1 to about 5 carbon atoms. In some other preferred embodiments the alkyl moieties of the alkanoyl groups have from about 1 to about 6 carbon atoms. Exemplary alkanoyl groups include, but are not limited to, acetyl (ethanoyl), n-propanoyl, n-butanoyl, 2-methylpropanoyl, n-pentanoyl, 2-methylbutanoyl, 3-methylbutanoyl, 2,2-dimethylpropanoyl, heptanoyl, and decanoyl. Alkanoyl groups can be optionally substituted.

As used herein, "cycloalkanoyl" refers to a —C(=O)-cycloalkyl group, wherein cycloalkyl is as previously defined. In some preferred embodiments the cycloalkyl moieties of the alkanoyl groups have from about 3 to about 8 carbon atoms. Exemplary cycloalkanoyl groups include, but are not limited to, cyclohexanoyl, cyclopropanoyl, cyclobutanoyl, 2-methylcyclopropanoyl, cyclopentanoyl, cycloheptanoyl, and cyclodecanoyl. Cycloalkanoyl groups can be optionally substituted.

As used herein, "alkoxycarbonyl" refers to a —C(=O)—O-alkyl group, wherein alkyl is as previously defined. In some preferred embodiments the alkyl moieties of the alkoxycarbonyl groups have from about 1 to about 6 carbon atoms. Exemplary alkoxycarbonyl groups include, but are not limited to, methoxycarbonyl, ethoxycarbonyl, n-propoxycarbonyl, i-propoxycarbonyl, n-butoxycarbonyl, and heptoxycarbonyl. Alkoxycarbonyl groups can be optionally substituted.

As used herein, "alkanoyloxy" refers to a —OC(=O)-alkyl group, wherein alkyl is as previously defined. In some preferred embodiments the alkyl moieties of the alkanoyloxy groups have from about 1 to about 5 carbon atoms. Exemplary alkanoyl groups include, but are not limited to, acetoxy (ethanoyloxy), n-propanoyloxy, n-butanoyloxy, 2-methylpropanoyloxy, n-pentanoyloxy, 2-methylbutanoyloxy, 3-methylbutanoyloxy, 2,2-dimethylpropanoyloxy, heptanoyloxy, and decanoyloxy. Alkanoyloxy groups can be optionally substituted.

As used herein, "halo" and "halogen" each refers to a fluoro, chloro, bromo, or iodo moiety attached to a compound of the invention. Preferably, "halo" and "halogen" refer to fluoro or chloro moieties.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), carboxy (—COOH), —O—C(=O)R", —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$NH$_2$, —S(=O)$_2$NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

"Side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, constipation, nausea and/or vomiting.

"Effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount", when used in connection with opioids, for example, for the treatment of pain, refers to the treatment and/or prevention of the painful condition. The term "effective amount", when used in connection with opioid antagonist compounds, refers to the treatment and/or prevention of side effects typically associated with opioids including, for example, such side effects as constipation, nausea and/or vomiting, as well as other side effects, discussed in further detail below.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with", "combination therapy" and "combination products" refer, in certain embodiments, to the concurrent administration to a patient of opioids and the compounds of formula (I). When administered in combination, each component may be administered at the same time or sequentially in any order at different points in time. Thus, each component may be administered separately but sufficiently closely in time so as to provide the desired therapeutic effect.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Patient" refers to animals, including mammals, preferably humans.

"Prodrug" refers to compounds specifically designed to maximize the amount of active species that reaches the desired site of reaction, which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The piperidines of the invention as illustrated in formula I can occur as the trans and cis stereochemical isomers at the 3- and 4-positions of the piperidine ring. The term "trans" as used herein refers to the $R^{2a}$ substituent being on the opposite side of the $R^{2b}$ substituent, whereas in the "cis" isomer, the $R^{2a}$ substituent and the $R^{2b}$ substituent are on the same side of the ring. The present invention contemplates the individual stereoisomers, as well as racemic mixtures. In the most preferred compounds of the present invention, the $R^{2a}$ substituent and the $R^{2b}$ substituent are in the "trans" orientation on the piperidine.

In addition to the "cis" and "trans" orientation of the $R^{2a}$ substituent and the $R^{2b}$ substituent, the absolute stereochemistry of the carbon atoms bearing the $R^{2a}$ substituent and the $R^{2b}$ substituent is also defined as using the commonly employed "R" and "S" definitions (Orchin et al., *The Vocabulary of Organic Chemistry*, 1980, John Wiley and Sons, Inc., page 126, which is incorporated herein by reference). The preferred compounds of the present invention are those of formula I in which the configuration of both the $R^{2a}$ substituent and the $R^{2b}$ substituent on the piperidine ring is "R".

Furthermore, asymmetric carbon atoms may be introduced into the molecule depending on the structure of:

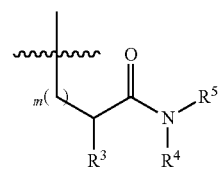

and the independent selection of any variables contained therein. For example, when $R^3$ is not hydrogen, the carbon atom to which $R^3$ is attached is asymmetric. Further, independent selection of $R^4$ or $R^5$, or independent sub-variables therein contained, may give rise to additional asymmetric centers. As such, these classes of compounds can exist as the individual "R" or "S" stereoisomers at each or any of these asymmetric centers, alone or in combination with any other asymmetric centers so formed in the compound to provide single enantiomers, or the racemic mixture of the isomers, or diastereomeric mixtures thereof, and all are contemplated as within the scope of the present invention. Preferably, a substantially pure stereoisomer of the compounds of this invention is used, i.e., an isomer in which the configuration at each of the asymmetric centers is independently "R" or "S". Preferably, those stereoisomers are compounds in which the chirality at each of the three asymmetric carbon centers bearing the $R^{2a}$, $R^{2b}$, and $R^3$ variables in compounds of formula I is (R).

Other asymmetric centers are contemplated in the present invention. For example, in compounds of formula VI, described in further detail below, $R^5$ is

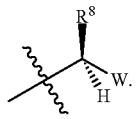

In certain preferred embodiments, the compounds, pharmaceutical compositions and methods of the present invention may involve a peripheral opioid antagonist compound. The term "peripheral" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5%, and most preferably 0%, of the pharmacological activity of the compounds employed in the present methods is exhibited in the CNS.

Furthermore, it is preferred in certain embodiments of the invention where the compound is administered to antagonize the peripheral side effects of an opioid that the compound does not substantially cross the blood-brain bather and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

Accordingly, in one embodiment, the present invention provides novel pharmaceutically active compounds of formula I:

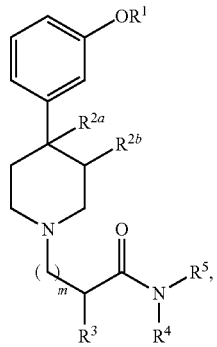

wherein:
$R^1$ is H or alkyl;
$R^{2a}$ is alkyl or alkenyl;
$R^{2b}$ is H, alkyl, or alkenyl;
$R^3$ is H, alkyl, alkenyl, aryl, cycloalkyl, cycloalkenyl, cycloalkylalkyl, cycloalkenylalkyl, or aralkyl;
$R^4$ is:
  H,
  aryl (optionally substituted by one or more substituents selected from —OH, nitro, halo, —CN, —CH$_2$CN, —C(=O)NH$_2$, —CO$_2$H, —N(R$^{6a}$)(R$^{6b}$), alkoxycarbonyl, aryloxy, aryl, alkyl, alkoxy, and alkanoyl (which latter three groups are optionally substituted by one or more halo atoms)),
  aralkyl;
  alkyl,
  alkenyl or
  alkynyl, which latter three groups are optionally substituted by one or more substituents selected from —OR$^{6c}$, —S(=O)$_q$R$^{6d}$, —CN, halo, alkoxycarbonyl, amino, alkanoyl, alkanoyloxy, cycloalkyl, cycloalkanoyl, —N(R$^{6e}$)S(=O)$_2$R$^{7a}$, —P(=O)OR$^{7b}$OR$^{7c}$, Het$^1$, and aryl (which latter group is optionally substituted by one or more substituents selected from —OH, nitro, —N(R$^{6a}$)(R$^{6b}$), halo, —CN, —CH$_2$CN, —C(=O)NH$_2$, —CO$_2$H, —CHO, aryl, alkyl, alkoxy, aralkoxy, aryloxy, and alkanoyl (which latter three groups are optionally substituted by one or more halo atoms));
$R^{6a}$, $R^{6b}$, $R^{6c}$, $R^{6d}$, and $R^{6e}$, are each independently H, Het$^2$, alkyl, alkenyl, alkynyl, cycloalkyl, aralkyl, or aryl (which latter six groups are optionally substituted by one or more substituents selected from OH, nitro, halo, —NHC(=O)R$^3$, —CN, —CH$_2$CN, —C(=O)NH$_2$, —CO$_2$H, alkoxycarbonyl, alkyl, alkoxy, and alkanoyl (which latter three groups are optionally substituted by one or more halo atoms));
$R^5$ is —(CH$_2$)$_y$(CHR$^8$)$_j$(CHR$^{8a}$)$_z$W, —CH$_2$P(=O)OR$^{7b}$OR$^{7c}$, or —S(=O)$_2$R$^{7d}$;
$R^8$ is each independently aryl (optionally substituted by one or more substituents selected from —OH, nitro, aryl, halo, —CN, —CH$_2$CN, —C(=O)NH$_2$, —CO$_2$H, —N(R$^{6a}$)(R$^{6b}$), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —OR$^{6c}$, —S(O)$_q$R$^{6d}$, —CN, halo, amino, —CO$_2$H, —C(=O)NH$_2$, alkoxycarbonyl, alkanoyl, alkanoyloxy, cycloalkyl, cycloalkanoyl, —N(R$^{6e}$)S(=O)$_2$R$^{7a}$, —P(=O)OR$^{7b}$OR$^{7c}$, Het$^1$, and aryl (which latter group is optionally substituted by one or more substituents selected from —OH, nitro, amino, halo, —CN, —CH$_2$CN, —C(=O)NH$_2$, —CO$_2$H, aroyl, aryl, alkyl, alkoxy, and alkanoyl (which latter three groups are optionally substituted by one or more halo atoms)); or R$^4$ and R$^8$ when taken together with the atoms through which they are connected, form a 4- to 8-membered heterocycloalkyl ring, wherein said heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N(R$^{11}$) groups;

R$^{8a}$ is each independently H, aryl (optionally substituted by one or more substituents selected from —OH, nitro, aryl, halo, —CN, —CH$_2$CN, —C(=O)NH$_2$, —CO$_2$H, —N(R$^{6a}$)(R$^{6b}$), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —OR$^{6c}$, —S(O)$_q$R$^{6d}$, —CN, halo, amino, —CO$_2$H, —C(=O)NH$_2$, alkoxycarbonyl, alkanoyl, alkanoyloxy, cycloalkyl, cycloalkanoyl, —N(R$^{6e}$)S(=O)$_2$R$^{7a}$, —P(=O)OR$^{7b}$OR$^{7c}$, Het$^1$, and aryl (which latter group is optionally substituted by one or more substituents selected from —OH, nitro, amino, halo, —CN, —CH$_2$CN, —C(=O)NH$_2$, —CO$_2$H, aroyl, aryl, alkyl, alkoxy, and alkanoyl (which latter three groups are optionally substituted by one or more halo atoms)); or R$^4$ and R$^{8a}$ when taken together with the atoms through which they are connected, form a 4- to 8-membered heterocycloalkyl ring, wherein said heterocycloalkyl ring is optionally fused to an aromatic ring, and wherein said heterocycloalkyl ring, or the aromatic ring to which is optionally fused, is each independently optionally substituted by one or more substituents selected from —OH, alkyl, or alkoxy; and wherein the heterocycloalkyl ring is also optionally interrupted by one or more O, S or N(R$^{11}$) groups;

W is —C(=O)OR$^9$, —C(=O)N(R$^{10a}$)(R$^{10b}$) or —P(=O)OR$^{7b}$OR$^{7c}$;

R$^9$ is H, alkyl, alkenyl, phenyl, cycloalkyl, cycloalkenyl, cycloalkylalkyl, cycloalkenylalkyl, or aralkyl;

R$^{10a}$ and R$^{10b}$, each independently represent H, alkyl, alkenyl, alkynyl, cycloalkyl, aralkyl, Het$^3$, or aryl (which latter seven groups are optionally substituted by one or more substituents selected from —OH, nitro, halo, —CN, —CH$_2$CN, —C(=O)NH$_2$, —CO$_2$H, alkyl, alkoxy, and alkanoyl (which latter three groups are optionally substituted by one or more halo atoms)); or R$^{10a}$ and R$^{10b}$ when taken together with the nitrogen atom to which they are attached form a 4- to 8-membered heterocycloalkyl ring, wherein said heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N(R$^{12}$) groups;

R$^{7a}$, R$^{7b}$, R$^{7c}$, and R$^{7d}$, are each independently H, alkyl, cycloalkyl, alkaryl, aralkyl or aryl, which latter five groups are optionally substituted by one or more substituents selected from alkyl, alkoxy, —OH, nitro, amino and halo;

Het$^1$, Het$^2$ and Het$^3$ each independently represent a 3- to 8-membered heterocyclic ring, wherein said heterocyclic ring contains at least one heteroatom selected from oxygen, sulfur and/or nitrogen, wherein said heterocyclic ring is optionally fused to an aromatic ring, and wherein said heterocyclic ring, or the aromatic ring to which it is optionally fused, is each independently optionally substituted by one or more substituents selected from —OH, =O, nitro, amino, halo, —CN, —CO$_2$H, aryl, alkyl, alkoxy and alkanoyl (which latter three groups are optionally substituted by one or more halo atoms);

R$^{11}$ represents H, alkyl, cycloalkyl, cycloalkylalkyl, or aralkyl;

R$^{12}$ represents H, alkyl, cycloalkyl, cycloalkylalkyl, or aralkyl;

j is the integer 0, 1, 2, 3, or 4;
m is the integer 0, 1, 2, 3, or 4;
q is the integer 0, 1, or 2;
y is the integer 0, 1, 2, 3, 4, or 5; and
z is the integer 0, 1, 2, 3, or 4;
with the proviso that when j and z are each the integer 0, y must be the integer 5;

or a stereoisomer, prodrug, pharmaceutically acceptable salt, hydrate, solvate, acid hydrate, N-oxide or isomorphic crystalline form thereof.

In certain embodiments of compounds of formula I, R$_1$ is alkyl or H. In certain preferred embodiments, R$^1$ is H.

In other embodiments of compounds of formula I, R$^{2a}$ is alkyl or alkenyl. More preferably, R$^{2a}$ is C$_1$-C$_5$ alkyl or C$_2$-C$_6$ alkenyl. More preferably still, R$^{2a}$ is C$_1$-C$_5$ alkyl. Most preferably, R$^{2a}$ is methyl.

In other embodiments of compounds of formula I, R$^{2b}$ is H, alkyl, or alkenyl. More preferably, R$^{2b}$ is alkyl or alkenyl. More preferably still, R$^{2b}$ is C$_1$-C$_5$ alkyl or C$_2$-C$_6$ alkenyl. Even more preferably, R$^{2b}$ is C$_1$-C$_5$ alkyl. Most preferably, R$^{2b}$ is methyl.

In certain embodiments of compounds of formula I, R$^{2a}$ and R$^{2b}$ are trans to each other. More preferably, one or more of R$^{2a}$ and R$^{2b}$ are independently C$_1$-C$_5$ alkyl, and R$^{2a}$ and R$^{2b}$ are trans to each other. More preferably, R$^{2a}$ and R$^{2b}$ are C$_1$-C$_5$ alkyl and R$^{2a}$ and R$^{2b}$ are trans to each other. Most preferably, R$^{2a}$ and R$^{2b}$ are methyl and R$^{2a}$ and R$^{2b}$ are trans to each other.

In other embodiments of compounds of formula I, R$^3$ is H, alkyl, alkenyl, aryl, cycloalkyl, cycloalkenyl, cycloalkylalkyl, cycloalkenylalkyl, or aralkyl. Preferably, R$^3$ is H, alkyl, or aralkyl. In some more preferred embodiments, R$^3$ is H.

In other more preferred embodiments, R$^3$ is aralkyl. Even more preferably, R$^3$ is benzyl. Most preferably, R$^3$ is:

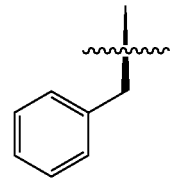

In other embodiments of the compound of formula I, R⁴ is:
H,
aryl (optionally substituted by one or more substituents selected from —OH, nitro, halo, —CN, —CH₂CN, —C(=O)NH₂, —CO₂H, —N(R⁶ᵃ)(R⁶ᵇ), alkoxycarbonyl, aryloxy, aryl, alkyl, alkoxy, and alkanoyl (which latter three groups are optionally substituted by one or more halo atoms)),
aralkyl;
alkyl,
alkenyl,
which latter three groups are optionally substituted by one or more substituents selected from —OR⁶ᶜ, —S(=O)_q R⁶ᵈ, —CN, halo, alkoxycarbonyl, amino, alkanoyl, alkanoyloxy, cycloalkyl, cycloalkanoyl, N(R⁶ᵉ)S(=O)₂R⁷ᵃ, —P(=O)OR⁷ᵇOR⁷ᶜ, Het¹, and aryl (which latter group is optionally substituted by one or more substituents selected from —OH, nitro, amino, —N(R⁶ᵃ)(R⁶ᵇ) halo, —CN, —CH₂CN, —C(=O)NH₂, —CO₂H, aryl, alkyl, alkoxy, aralkoxy, aryloxy, and alkanoyl (which latter three groups are optionally substituted by one or more halo atoms)).

In some preferred embodiments, R⁴ is H. In other preferred embodiments, R⁴ is:
aryl (optionally substituted by one or more substituents selected from alkoxycarbonyl, aryloxy, aryl, and alkoxy (which latter group is optionally substituted by one or more halo atoms));
aralkyl;
alkyl, optionally substituted with cycloalkyl or amino; or
alkenyl.

In some other embodiments of the compounds of formula I:
R⁶ᵃ, R⁶ᵇ, R⁶ᶜ, R⁶ᵈ, and R⁶ᵉ, are each independently H, Het², alkyl, alkenyl, alkynyl, cycloalkyl, aralkyl, or aryl (which latter six groups are optionally substituted by one or more substituents selected from OH, nitro, halo, —NHC(=O)R³, —CN, —CH₂CN, —C(=O)NH₂, —CO₂H, alkoxycarbonyl, alkyl, alkoxy, and alkanoyl (which latter three groups are optionally substituted by one or more halo atoms));

In certain embodiments of the compounds of formula I, R⁵ is —(CH₂)_y(CHR⁸)_j(CHR⁸ᵃ)_zW, —CH₂P(=O)OR⁷ᵇOR⁷ᶜ, or —S(=O)₂R⁷ᵈ. In more preferred embodiments, R⁵ is —S(=O)₂R⁷ᵈ. In more preferred embodiments, R⁵ is —CH₂P(=O)OR⁷ᵇOR⁷ᶜ. In yet other more preferred embodiments, R⁵ is —(CH₂)_y(CHR⁸)_j(CHR⁸ᵃ)_zW. In some more preferred embodiments, R⁵ is:

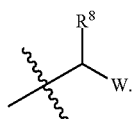

In still more preferred embodiments, R⁵ is:

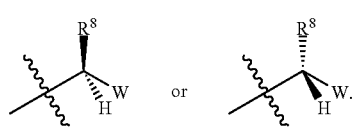

In even more preferred embodiments, R⁵ is:

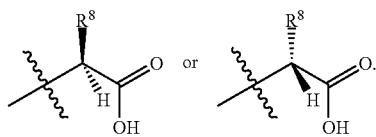

In some embodiments of the compounds of formula I, each R⁸ is independently aryl (optionally substituted by one or more substituents selected from —OH, nitro, aryl, halo, —CN, —CH₂CN, —C(=O)NH₂, —CO₂H, —N(R⁶ᵃ)(R⁶ᵇ), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —OR⁶ᶜ, —S(O)_qR⁶ᵈ, —CN, halo, amino, —CO₂H, —C(=O)NH₂, alkoxycarbonyl, alkanoyl, alkanoyloxy, cycloalkyl, cycloalkanoyl, —N(R⁶ᵉ)S(=O)₂R⁷ᵃ, —P(=O)OR⁷ᵇOR⁷ᶜ, Het¹, and aryl (which latter group is optionally substituted by one or more substituents selected from —OH, nitro, amino, halo, —CN, —CH₂CN, —C(=O)NH₂, —CO₂H, aroyl, aryl, alkyl, alkoxy, and alkanoyl (which latter three groups are optionally substituted by one or more halo atoms)). In some preferred embodiments, each R⁸ is independently aryl, cycloalkyl, alkyl, wherein the alkyl group is optionally substituted by one or more substituents selected from —OR⁶ᶜ, —S(O)_qR⁶ᵈ, amino, —CO₂H, —C(=O)NH₂, cycloalkyl, —N(R⁶ᵉ)S(=O)₂R⁷ᵃ, Het¹, and aryl (which latter group is optionally substituted by one or more substituents selected from —OH, nitro, halo, aroyl, and aryl. In certain more preferred embodiments, R⁸ is alkyl substituted with aryl in which the aryl is optionally substituted by one or more substituents selected from —OH, nitro, fluoro, iodo, benzoyl, and phenyl). In even more preferred embodiments, R⁸ is methyl or ethyl, substituted with phenyl, α-naphthyl, or β-naphthyl, the latter three groups optionally substituted by one or more substituents selected from —OH, nitro, fluoro, iodo, benzoyl, and phenyl).

In some other embodiments of the compounds of formula I, R⁴ and R⁸ when taken together with the atoms through which they are connected, form a 4- to 8-membered heterocycloalkyl ring, wherein said heterocycloalkyl ring is optionally fused to an aromatic ring, and wherein the heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N(R¹¹) groups. In certain preferred embodiments, R⁴ and R⁸ when taken together with the atoms through which they are connected, form a 5- to 6-membered heterocycloalkyl ring, wherein the heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N(R¹¹) groups. In other preferred embodiments, R⁴ and R⁸ when taken together with the atoms through which they are connected, form a 5-membered heterocycloalkyl ring wherein the heterocycloalkyl ring is optionally substituted by —OH. In other preferred embodiments, R⁴ and R⁸ when taken together with the atoms through which they are connected, form a 6 membered heterocycloalkyl ring wherein the heterocycloalkyl ring is fused to an aromatic ring.

In certain embodiments of the compounds of formula I, each $R^{8a}$ is independently H, aryl (optionally substituted by one or more substituents selected from —OH, nitro, aryl, halo, —CN, —CH$_2$CN, —C(=O)NH$_2$, —CO$_2$H, —N($R^{6a}$)($R^{6b}$), alkyl, alkoxy, and alkanoyl (which latter three groups are optionally substituted by one or more halo atoms)), cycloalkyl, alkyl, alkenyl or alkynyl wherein said alkyl, alkenyl or alkynyl groups are optionally substituted by one or more substituents selected from —OR$^{6c}$, —S(O)$_q$R$^{6d}$, —CN, halo, amino, —CO$_2$H, —C(=O)NH$_2$, alkoxycarbonyl, alkanoyl, alkanoyloxy, cycloalkyl, cycloalkanoyl, —N($R^{6e}$)S(=O)$_2$R$^{7a}$, —P(=O)OR$^{7b}$OR$^{7c}$, Het$^1$, and aryl (which latter group is optionally substituted by one or more substituents selected from —OH, nitro, amino, halo, —CN, —CH$_2$CN, —C(=O)NH$_2$, —CO$_2$H, aroyl, aryl, alkyl, alkoxy, and alkanoyl (which latter three groups are optionally substituted by one or more halo atoms)); or $R^4$ and $R^{8a}$ when taken together with the atoms through which they are connected, form a 4- to 8-membered heterocycloalkyl ring, wherein said heterocycloalkyl ring is optionally fused to an aromatic ring, and wherein said heterocycloalkyl ring, or the aromatic ring to which is optionally fused, is each independently optionally substituted by one or more substituents selected from —OH, alkyl, or alkoxy; and wherein the heterocycloalkyl ring is also optionally interrupted by one or more O, S or N($R^{11}$) groups.

In certain embodiments of the compounds of formula I, W is —C(=O)OR$^9$, —C(=O)N($R^{10a}$)($R^{10b}$), or —P(=O)OR$^{7b}$OR$^{7c}$. In certain preferred embodiments, W is —C(=O)OR$^9$. More preferably, when W is —C(=O)OR$^9$, $R^9$ is H. In certain other preferred embodiments, W is —C(=O)N($R^{10a}$)($R^{10b}$). In some other preferred embodiments, W is —P(=O)OR$^{7b}$OR$^{7c}$. More preferably, when W is —P(=O)OR$^{7b}$OR$^{7c}$, $R^{7b}$ and $R^{7c}$ are both H.

In certain embodiments of the compounds of formula I, $R^9$ is H, alkyl, alkenyl, phenyl, cycloalkyl, cycloalkenyl, cycloalkylalkyl, cycloalkenylalkyl), or aralkyl. Preferably, $R^9$ is H.

In other embodiments of the compounds of formula I, $R^{10a}$ and $R^{10b}$, each independently represent H, alkyl, alkenyl, alkynyl, cycloalkyl, aralkyl, Het$^3$, or aryl (which latter seven groups are optionally substituted by one or more substituents selected from —OH, nitro, halo, —CN, —CH$_2$CN, —C(=O)NH$_2$, —CO$_2$H, alkyl, alkoxy, and alkanoyl (which latter three groups are optionally substituted by one or more halo atoms)); or $R^{10a}$ and $R^{10b}$ when taken together with the nitrogen atom to which they are attached form a 4- to 8-membered heterocycloalkyl ring wherein said heterocycloalkyl ring is optionally fused to an aromatic ring, and wherein said heterocycloalkyl ring, or the aromatic ring to which it is optionally fused, is each independently optionally substituted by one or more substituents selected from —OH, alkyl, or alkoxy; and wherein the heterocycloalkyl ring is also optionally interrupted by one or more O, S or N($R^{12}$) groups. More preferably, $R^{10a}$ and $R^{10b}$ are each selected independently from H and alkyl, wherein the alkyl is optionally substituted by one or more halo atoms.

In some embodiments of the compounds of formula I, $R^{7a}$, $R^{7b}$, $R^{7c}$, and $R^{7d}$ are each independently H, alkyl, cycloalkyl, alkaryl, aralkyl, or aryl, which latter five groups are optionally substituted by one or more substituents selected from alkyl, alkoxy, —OH, nitro, amino and halo. In some preferred embodiments, one or more $R^{7b}$ and $R^{7c}$ are each independently H. More preferably, $R^{7b}$ and $R^{7c}$ are both H. In other embodiments, $R^{7d}$ is alkyl, optionally substituted by one or more halo atoms. More preferably, $R^{7d}$ is alkyl, optionally substituted by one or more fluoro atoms. Still more preferably, $R^{7d}$ is —CF$_3$.

In other embodiments of the compounds of formula I, Het$^1$, Het$^2$ and Het$^3$ each independently represent a 3- to 8-membered heterocyclic ring, wherein said heterocyclic ring contains at least one heteroatom selected from oxygen, sulfur and/or nitrogen, wherein said heterocyclic ring is optionally fused to an aromatic ring, and wherein said heterocyclic ring, or the aromatic ring to which it is optionally fused, is each independently optionally substituted by one or more substituents selected from —OH, =O, nitro, amino, halo, —CN, —CO$_2$H, aryl, alkyl, alkoxy and alkanoyl (which latter three groups are optionally substituted by one or more halo atoms). In certain preferred embodiments, Het$^1$ is:

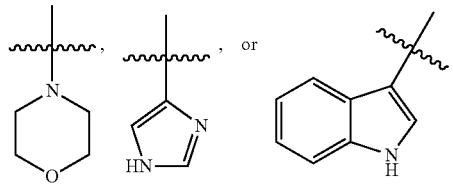

In still other embodiments of the compounds of formula I, $R^{11}$ represents H, alkyl, cycloalkyl, cycloalkylalkyl or aralkyl.

In yet other embodiments of the compounds of formula I, $R^{12}$ represents H, alkyl, cycloalkyl, cycloalkylalkyl or aralkyl.

In still other embodiments of the compounds of formula I, j is the integer 0, 1, 2, 3, or 4; m is the integer 0, 1, 2, 3, or 4; q is the integer 0, 1, or 2; y is the integer 0, 1, 2, 3, 4, or 5; and z is the integer 0, 1, 2, 3, or 4; with the proviso that when j and z are each the integer 0, y must be the integer 5. In certain preferred embodiments, j is the integer 1. In certain other preferred embodiments, m is the integer 1. In still other preferred embodiments, y is the integer 5.

In certain preferred embodiments of the present invention, the compounds of formula I have the structure corresponding to formula II:

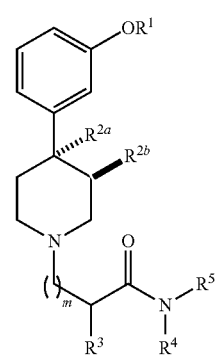

wherein $R^1$, $R^{2a}$, $R^{2b}$, $R^3$, $R^4$, $R^5$, and m are as set forth above. In more preferred embodiments, $R^{2a}$ and $R^{2b}$ are each methyl.

Alternatively, the compounds of formula I have the structure corresponding to formula III:

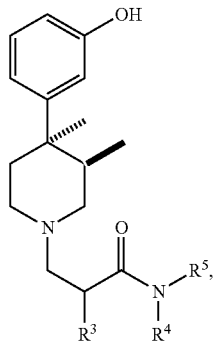

III wherein $R^3$ is H, alkyl, or aralkyl, and $R^4$ and $R^5$ are as set forth above.

In certain embodiments, the compounds of formula I have the structure corresponding to formula IV:

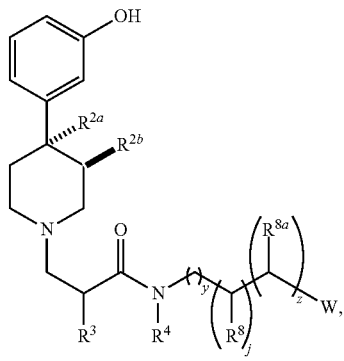

IV wherein $R^3$ is H, alkyl, or aralkyl, and $R^{2a}$, $R^{2b}$, $R^4$, $R^8$, $R^{8a}$, W, y, j, and z are as set forth above. In some preferred embodiments of compounds of formula IV, $R^4$ is H. In other preferred embodiments of compounds of formula IV, $R^3$ is:

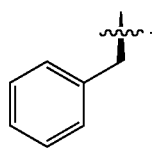

In certain other embodiments, the compounds of formula I have the structure corresponding to formula V:

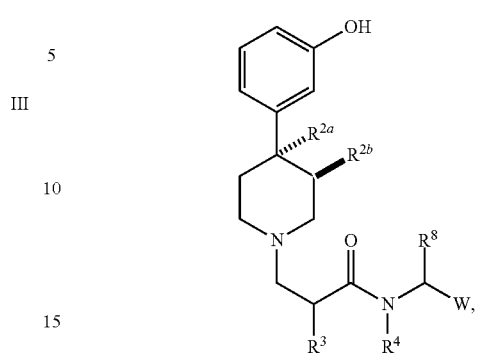

V wherein $R^3$ is H, alkyl, or aralkyl, and $R^{2a}$, $R^{2b}$, $R^4$, $R^8$, and W are as set forth above. In some preferred embodiments of compounds of the formula V, $R^4$ is H. In other preferred embodiments, the compounds of the formula V have the structure corresponding to formula VIa or formula VIb:

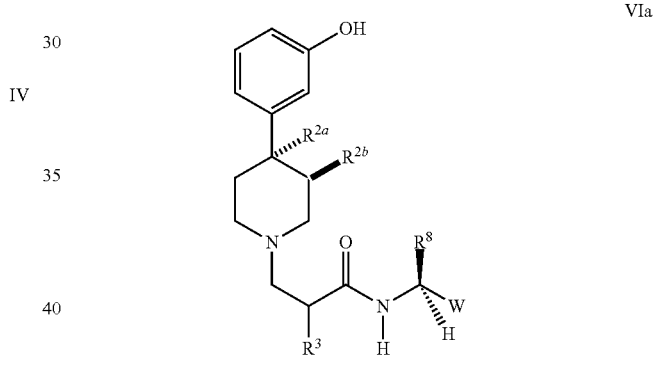

VIa

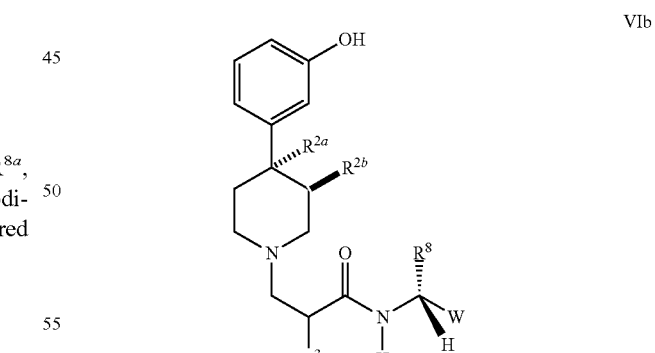

VIb wherein $R^3$ is H, alkyl, or aralkyl, and $R^{2a}$, $R^{2b}$, $R^8$, and W are as set forth above. In some preferred embodiments of compounds of formula VIa and formula VIb, W is —$CO_2H$, and $R^{2a}$ and $R^{2b}$ are each methyl. In certain more preferred embodiments of the compounds of formula VIa and formula VIb, wherein W is —$CO_2H$, and $R^{2a}$ and $R^{2b}$ are each methyl, $R^3$ is:

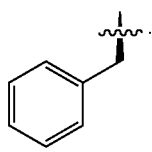

In certain more preferred embodiments of compounds of formula VIa and formula VIb, wherein W is —CO²H, and R$^{2a}$ and R$^{2b}$ are each methyl, and R$^3$ is:

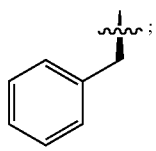

R$^4$ is H.

In other more preferred embodiments of compounds of formula VI, wherein W is —CO²H, and R$^{2a}$ and R$^{2b}$ are each methyl, R$^8$ is alkyl substituted with aryl, optionally substituted by one or more substituents selected from —OH, nitro, amino, halo, —CN, —CH$_2$CN, —C(=O)NH$_2$, —CO$_2$H, aroyl, aryl, —N(R$^{6a}$)(R$^{6b}$), alkyl, alkoxy, and alkanoyl (which latter three groups are optionally substituted by one or more halo atoms). Even more preferably, R$^8$ is optionally substituted benzyl. Even more preferably, said benzyl is substituted by one or more substituents selected from —OH, nitro, halo, aroyl, or aryl.

In certain preferred embodiments, the compounds of formula V have the structure corresponding to formula VII:

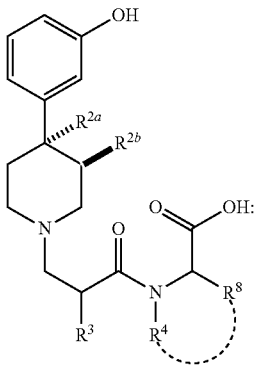

VII wherein R$^{2a}$, R$^{2b}$, R$^3$, R$^4$, and R$^8$ are as set forth above. In more preferred compounds of formula VII, R$^3$ is:

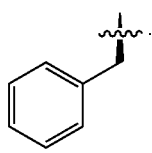

Even more preferably, in compounds of formula VII, R$^{2a}$ and R$^{2b}$ are each methyl, and R$^3$ is as set forth directly above.

More preferably still, the compounds of formula VII have the structure corresponding to formula VIIa or formula VIIb:

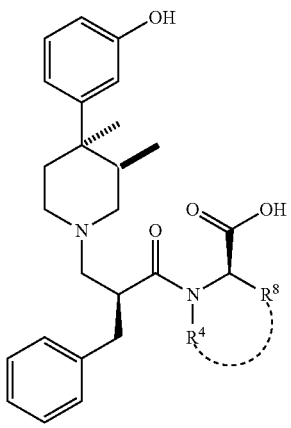

VIIa

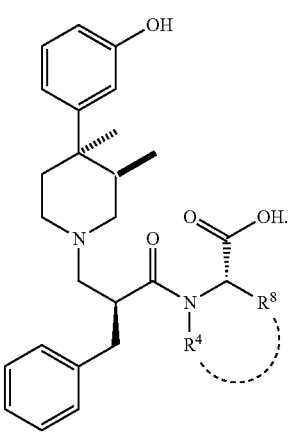

VIIb

In certain preferred embodiments of the present invention, the compounds of formula I have the structure corresponding to formula VIII:

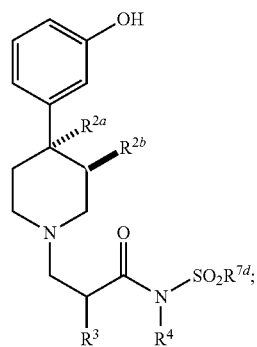

VIII wherein R$^3$ is H, alkyl, or aralkyl, and R$^{2a}$, R$^{2b}$, R$^4$, and R$^{7d}$ are as set forth above.

In certain preferred embodiments of the present invention, the compounds of formula I have the structure corresponding to formula IX:

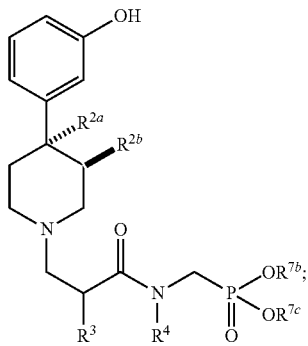

IX wherein $R^3$ is H, alkyl, or aralkyl, and $R^{2a}$, $R^{2b}$, $R^4$, $R^{7b}$ and $R^{7c}$ are as set forth above.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 3d. Ed., Wiley & Sons, 1991.

The 3,4-disubstituted-4-aryl piperidine compounds according to the present invention may be synthesized employing methods taught, for example, in U.S. Pat. Nos. 5,250,542, 5,434,171, 5,159,081, and 5,270,328, the disclosures of which are hereby incorporated herein by reference in their entireties. The optically active (+)-4(R)-(3-hydroxyphenyl)-3(R),4-dimethyl-1-piperidine was employed as starting material in the synthesis of the present compounds may be prepared by the general procedure taught in *J. Org. Chem.*, 1991, 56, 1660-1663, U.S. Pat. Nos. 4,115,400 and 4,891,379, the disclosures of which are hereby incorporated herein by reference in their entireties.

While not intending to be bound by any theory or theories of operation, it is contemplated that opioid side effects, such as constipation, vomiting and nausea, may result from undesirable interaction of the opioid with peripheral opioid receptors, such as peripheral μ receptors. Administration of the compounds of formula I according to one aspect of the present invention may block interaction of the opioid compounds with the peripheral receptors, thereby preventing and/or inhibiting the side effects, while preferably not interfering with the therapeutic effect of the opioid in the CNS.

When any variable occurs more than one time in any constituent or in any formula, its definition in each occurrence is independent of its definition at every other occurrence. Combinations of substituents and/or variables are permissible only if such combinations result in stable compounds.

In accordance with certain embodiments of the present invention, there are provided methods that comprise administering to a patient, inter alia, an opioid compound. A wide variety of opioids is available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl, tramadol, and mixtures thereof.

The opioid component of the present compositions may further include one or more other active ingredients that may be conventionally employed in analgesic and/or cough-coldantitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain,* 1996, 67, 361), L-364,718 and other CCK antagonists (Dourish, C. T. et al., *Eur. J. Pharmacol.,* 1988, 147, 469), NOS inhibitors (Bhargava, H. N. et al., *Neuropeptides,* 1996, 30, 219), PKC inhibitors (Bilsky, E. J. et al., *J. Pharmacol. Exp. Ther.,* 1996, 277, 484), and dynorphin antagonists or antisera (Nichols, M. L. et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Another embodiment of the invention provides a pharmaceutical composition comprising a pharmaceutically acceptable carrier and an effective amount of a compound of formula I.

Yet another embodiment of the invention provides a method for treating or preventing opioid-bowel dysfunction comprising the step of administering to a patient in need of such treatment a composition comprising an opioid and an effective amount of a compound of formula I.

Still another embodiment of the invention provides a method for treating or preventing ileus comprising the step of administering to a patient in need of such treatment, an effective amount of a compound of formula I.

Another embodiment of the invention provides a method for treating or preventing a side effect associated with an opioid comprising the step of administering to a patient, an effective amount of a compound of formula I.

Although the compounds of the present invention may be administered as the pure chemicals, it is preferable to present the active ingredient as a pharmaceutical composition. The invention thus further provides a pharmaceutical composition comprising one or more of the compounds of formula I, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

The compounds of the invention may be administered in an effective amount by any of the conventional techniques well-established in the medical field. The compounds employed in the methods of the present invention including, for example, opioid and the compounds of formula I, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products of this invention, such as pharmaceutical compositions comprising opioids in combination with the compounds of formula I, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the opioid compounds and the compounds of formula I may be administered at the same time (that is, together), or in any order. When not administered at the same time, preferably the administration of an opioid and the compounds of formula I occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the opioids and the compounds of formula I are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compounds is combined with the compounds of formula I, for example, typically a daily dosage may range from about 0.01 to about 100 milligrams of the opioid (and all combinations and subcombinations of ranges therein) and about 0.001 to about 100 milligrams of the compounds of formula I (and all combinations and subcombinations of ranges therein), per kilogram of patient body weight. Preferably, the a daily dosage may be about 0.1 to about 10 milligrams of the opioid and about 0.01 to about 10 milligrams of the compounds of formula I per kilogram of patient body weight. Even more preferably, the daily dosage may be about 1.0 milligrams of the opioid and about 0.1 milligrams of the compounds of formula I per kilogram of patient body weight. With regard to a typical dosage form of this type of combination product, such as a tablet, the opioid compounds (e.g., morphine) generally may be present in an amount of about 15 to about 200 milligrams, and the compounds of formula I in an amount of about 0.1 to about 4 milligrams.

Particularly when provided as a single dosage form, the potential exists for a chemical interaction between the combined active ingredients (for example, an opioid and the compounds of formula I). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the treatment of pain, which comprise a therapeutically effective amount of an opioid along with a therapeutically effective amount of the 3,4-disubstituted-4-aryl-piperidine compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid compound and the compounds of formula I may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds of the present invention may be used in methods to bind opioid receptors, including μ and κ opioid receptors. Such binding may be accomplished by contacting the receptor with an effective amount of the compound of the invention. Preferably, the contacting step conducted in an aqueous medium, preferably at physiologically relevant ionic strength, pH, and the like.

In certain preferred embodiments, the compounds of the present invention bind μ and κ opioid receptors or combinations thereof. The opioid receptors may be located in the central nervous system or located peripherally to the central nervous system or in both locations.

In certain other preferred embodiments, the compounds of the present invention bind κ opioid receptors.

In preferred embodiments of the methods of the invention, the compounds antagonize the activity of the opioid receptors. In other preferred embodiments, the compounds prevent or treat a condition or disease caused by an opioid (either endogenous or exogenous). In certain embodiments of the method, particularly where the opioid are exogenous, the compounds of the invention preferably do not substantially cross the blood-brain barrier.

The compounds of the present invention may be used in methods to antagonize μ, κ or both types of opioid receptors, particularly where undesirable symptoms or conditions are side effects of administering exogenous opioids. Furthermore, the compounds of the invention may be used as to treat patients having disease states that are ameliorated by binding opioid receptors or in any treatment wherein temporary suppression of the μ, κ or both types of opioid receptor system is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); prevention of sudden infant death syndrome; treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the invention present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain preferred embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

In certain preferred embodiments, the compounds of the invention may be used in methods for preventing or treating post-operative or opioid-induced ileus.

In other preferred embodiments, the compounds of the invention may be used in an effective amount in a method in combination with an effective amount of an opioid to treat pain.

The compounds of the invention may be administered before, during or after administering at least one opioid. The methods of the invention are particularly effective for opioids selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

Employing the methodology herein described or cited, N-substituted-(3-substituted phenyl)-3,4-disubstituted-1-piperidine compounds of formula I can be readily prepared. The invention is further described in the following examples. The actual examples, herein provided, are for illustrative purposes only, and are not to be construed as limiting the appended claims. They provide a series of N-substituted (+)-4(R)-(3-substituted phenyl)-3(R),4-dimethyl-1-piperidine derivatives of Formulae V and VII, prepared according to Schemes 1-5, shown below.

The Examples 1 and 6 to 36 listed in Table 1 were prepared according to the Scheme 1. Fmoc-protected α-amino acids linked to Wang resin (1), purchased from Advanced Chemtech, were used as starting material for the synthesis of derivatives of general formula 5. Treatment of 1 with piperidine/DMF afforded the resin-bound Fmoc deprotected α-amino acids 2 which were coupled to the acid 3[Werner et al., *J. Org. Chem.*, 1996, 61, 587-597] using HATU as coupling agent. The reaction time (3 hours) and number of equivalents of each reagent were critical in order to obtain good conversion of the desired coupled product 4 while minimizing the formation of the O-acylation side products. Cleavage of the resin 4 using trifluoroacetic acid gave the desired carboxylic acid derivatives. Under the acidic cleavage conditions, all Boc, tert-butyl, and trityl protecting groups (R1 substituents) were simultaneously removed to generate the corresponding primary or secondary amines, carboxylic acids, alcohols, indoles, imidazoles, and carboxamides. The purity of cleaved products was generally >50% as determined by LCMS and compounds were purified to >98% purity by routine HPLC.

Alternatively, the Fmoc-protected α-amino acids may be prepared by known techniques (such as those disclosed in Greene, T. W. and Wuts, P. G. M., *Protective Groups in Organic Synthesis* 3d. Ed., Wiley & Sons, 1999) and then attached to the Wang resin using standard coupling procedures (such as those disclosed in Bryan et al., *Tetrahedron Letters*, 2000, 41, 6997-7000; Burkett et al., *Tetrahedron Letters*, 2000, 41, 6661-6664.

The derivatives of general formula 9 (Examples 2 and 37 to 66) were prepared by a procedure (Scheme 2) analogous to that shown in Scheme 1. Coupling of 2 with the carboxylic acid 7, obtained by hydrolysis under basic conditions of the methyl ester 6[Werner et al., *J. Org. Chem.*, 1996, 61, 587-597], afforded the resin 8 which was cleaved using trifluoroacetic acid to give the carboxylic acid derivatives 9. As mentioned previously, under the acidic cleavage conditions, all Boc, tert-butyl and trityl protecting groups were simultaneously removed to generate the corresponding primary or secondary amines, carboxylic acids, alcohols, indoles, imidazoles and carboxamides. The purity of cleaved products was generally >50% as determined by LCMS and compounds were purified to >98% purity by routine HPLC.

The derivatives of general formula 14 (Examples 3, 67-70) were prepared according to Scheme 3. The reductive amination of the primary amine of the α-amino acid linked to Wang resin (2), using previously reported strategy [Matthews et al. *J. Org. Chem.*, 1997, 62, 6090-6092] provided the secondary amine intermediates 10. Coupling of resins 10 with acryloyl chloride in the presence of triethylamine provided the resin-bound acrylamide derivatives 11 which reacted with (+)-4(R)-(3-hydroxyphenyl)-3 (R),4-dimethyl-1-piperidine (12) [*J. Org. Chem.*, 1991, 56, 1660-1663] to give the desired 1,4-addition products 13. The resin intermediates 13 were cleaved using trifluoroacetic acid to give the carboxylic acid derivatives 14. The purity of cleaved products was generally >50% as determined by LCMS and compounds were purified to >98% purity by routine preparative HPLC.

The derivatives of general formula 20 (Examples 4, 71-78) were prepared according to the Scheme 4. The secondary amine derivatives 17 were obtained using a solid-phase variant of the Fukuyama-Mitsunobu process [Piscopio et al. *Tetrahedron Lett.*, 1998, 39, 2667-2670; Piscopio et al. *Tetrahedron*, 1999, 55, 8189-8198; Yang et al. *Tetrahedron Lett.*, 1997, 38, 7307-7310]. Hence, 2,4-dinitrosulfonamides 15, prepared from resin 2 and 2,4-dinitrobenzenesulfonyl chloride, can be alkylated efficiently under the Mitsunobu conditions (ROH, DIAD, $Ph_3P$, THF) to give the N,N-disubstituted 2,4-dinitrobenzenesulfonamides 16. Facile deprotection of 16 using n-butylamine provided the secondary amine intermediates 17. Coupling of resins 17 with acryloyl chloride in the presence of diisopropylethylamine provided the resin-bound acrylamide derivatives 18 that reacted with (+)-4(R)-(3-hydroxyphenyl)-3(R),4-dimethyl-1-piperidine (12) to give the 1,4-addition products 19. The resin intermediates 19 were cleaved using trifluoroacetic acid to give the carboxylic acid derivatives 20. The purity of cleaved products was generally >50% as determined by LCMS and compounds were purified to >98% purity by routine HPLC.

The derivatives of general formula 24 (Examples 5, 79, 80) were prepared according to the Scheme 5. The N-arylation of the resin-bound Fmoc deprotected α-amino acids 2 was conducted according to the method described by Combs and collaborators [Combs et al., *J. Comb. Chem.* 2002, 4, 179-182] ($ArB(OH)_2$, $Cu(OAc)_2$, $Et_3N$, THF). Coupling of the resulting resins 21 with acryloyl chloride in the presence of triethylamine provided the resin-bound acrylamide derivatives 22 which reacted with (+)-4(R)-(3-hydroxyphenyl)-3 (R),4-dimethyl-1-piperidine (12) to give the 1,4-addition products 23. The resin intermediates 23 were cleaved using trifluoroacetic acid to give the carboxylic acid derivatives 24. The initial purity of final products was generally >50% as determined by LCMS and compounds were purified to >98% purity by routine HPLC.

(1) EXPERIMENTAL SECTION

Materials: all chemicals were reagent grade and used without further purification. LC-MS data were obtained using a LC Thermo Finnigan Surveyor-MS Thermo Finnigan AQA in either positive mode or negative mode. Solvent A: 10 mM ammonium acetate, pH 4.5; solvent B: acetonitrile; solvent C: methanol; solvent D: water; column Waters Xterra C18 MS 2.0×50 mm, detector: PDA λ=220-300 nM. Gradient program (positive mode): t=0.00, 600 μL/min, 99% A-1% B; t=0.30, 600 μL/min, 99% A-1% B; t=5.00, 600 μL/min, 1% A-99% B; t=5.30, 600 μL/min, 1% A-99% B. Gradient program (negative mode): t=0.00, 600 μL/min, 9% A-1% B-90% D; t=0.30, 600 μL/min, 9% A-1% B-90% D; t=5.00, 600 μL/min, 99% B-1% D; t=5.30, 600 μL/min, 99% B-1% D.

Example 1

2(S)-{2(S)-Benzyl-3-[4(R)-(3-hydroxy-phenyl)-3 (R),4-dimethyl-piperidin-1-yl]-propionylamino}-3-phenyl-propionic acid (5a)

A solution dimethylformamide/piperidine 20:80 (20 mL) was added to the Fmoc-Phe Wang resin 1a (0.8 mmol/g, 0.250 g, 0.0002 mol) and the suspension was mixed at room temperature for 20 minutes (Scheme 1). The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of the resulting resin 2a in a mixture dichloromethane/dimethylformamide 1:1 (20 mL) was added consecutively diisopropylethylamine (0.036 mL, 0.00021 mol, 1.05 eq), carboxylic acid 3 (0.081 g, 0.00021 mol, 1.05 eq), and HATU (0.080 g, 0.00021 mol, 1.05 eq). The mixture was shaken for 3 h at room temperature. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. The resin 4a was shaken in a mixture trifluoroacetic acid/dichloromethane (1:1) (10 mL) at room temperature for 20 min. The filtrate was collected and the resin was further washed with dichloromethane (3×2 mL). Evaporation of the filtrate afforded the desired compound further purified by routine HPLC. For Example 1 (5a), $R^8$=(S) $CH_2Ph$; Mass spectral analysis: m/z=515 $(M+H)^+$.

Example 2

2(S)-{3-[4(R)-(3-Hydroxy-phenyl)-3(R),4-dimethyl-piperidin-1-yl]-propionylamino}-3-phenyl-propionic acid (9a)

Preparation of carboxylic acid derivative 7:

A 1N solution of aqueous sodium hydroxide (58.2 mL, 0.05821 mol, 3 eq) was added drop wise to a cold (0° C.) solution of 6 (5.65 g, 0.01940 mol, 1 eq) in tetrahydrofuran (100 mL). The mixture was allowed to warm to room temperature and stirring was continued for 16 h at room temperature. A 12N aqueous HCl solution (4.85 mL, 0.0582 mol, 3 eq) was added to neutralize the mixture that was concentrated under vacuum. The resulting solid was suspended in a mixture dichloromethane/MeOH 98:2. The mixture was filtered and the filtrate was evaporated to afford the desired compound 7 (3.7 g, 69%) used for the next step without further purification. Mass spectral analysis: m/z=278 $(M+H)^+$.

To a suspension of the resin 2a (preparation described in example 1) in a mixture dichloromethane/dimethylformamide 1:1 (20 mL) was added consecutively diisopropylethylamine (0.035 mL, 0.0002 mol, 1 eq), carboxylic acid 7 (0.056 g, 0.0002 mol, 1 eq), and HATU (0.076 g, 0.0002 mol, 1 eq). The mixture was shaken for 6 hours at room temperature. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. The resin 8a was shaken in a mixture trifluoroacetic acid/dichloromethane (1:1) (10 mL) at room temperature for 20 minutes. The filtrate was collected and the resin was further washed with dichloromethane (3×2 mL). Evaporation of the filtrate afforded the desired compound further purified by routine HPLC. For Example 2 (9a), $R^8$=(S)$CH_2Ph$; Mass spectral analysis: m/z=425 $(M+H)^+$.

Example 3

2(S)-[{3-[4(R)-(3-Hydroxy-phenyl)-3(R),4-dimethyl-piperidin-1-yl]-propionyl}-(4-methoxy-benzyl)-amino]-3-phenyl-propionic acid (14a)

To the resin 2a (0.00015 mol) swelled in trimethylorthoformate (6 mL) was added 4-methoxybenzaldehyde (0.408 g, 0.003 mol, 20 eq) and the reaction was mixed at room temperature for 30 min Sodium cyanoborohydride (0.190 g, 0.003 mol, 20 eq) dispersed in trimethylorthoformate (3 mL) was added followed by acetic acid (0.032 mL), and the reaction mixture was mixed for an additional 10 min at room temperature. The reaction was filtered and the resin was washed with dimethylformamide (5×), methanol (5×), dichloromethane/triethylamine 9:1 (5×), methanol (5×), dichloromethane (5×), methanol (5×), diethyl ether (5×) and dried under vacuum. To a suspension of the resin 10a obtained previously in dichloromethane (20 mL) was added triethylamine (2.1 mL, 0.0015 mol, 10 eq) followed by acryloyl chloride (0.12 mL, 0.0015 mol, 10 eq). The mixture was shaken at room temperature for 6 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of resin 11a obtained previously in MeOH/THF 1:2 (20 mL) was added (+)-4(R)-(3-hydroxyphenyl)-3 (R),4-dimethyl-1-piperidine (12) (46 mg, 0.00022 mol, 1.5 eq) and the mixture was stirred at room temperature for 12 hours. The resin was then drained, washed consecutively with dimethylformamide (5×), dimethylformamide/water (9:1) (5×), dimethylformamide (5×), methanol (5×), dichloromethane (5×) and re-suspended in MeOH/THF 1:2 (20 mL). (+)-4(R)-(3-hydroxyphenyl)-3(R),4-dimethyl-1-piperidine (12) (46 mg, 0.00022 mol, 1.5 eq) was added to the mixture which was stirred at room temperature for an additional 12 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. The resin 13a was shaken in a mixture trifluoroacetic acid/dichloromethane (1:1) (10 mL) at room temperature for 20 min. The filtrate was collected and the resin was further washed with dichloromethane (3×2 mL). Evaporation of the filtrate afforded the desired compound further purified by routine HPLC. For Example 3 (14a), $R^8$=(S)$CH_2$Ph; $R^4$=para-methoxybenzyl, $R^3$=H; Mass spectral analysis: m/z=545 (M+H)$^+$.

Example 4

(S)-(Ethyl-{3-[4(R)-(3-hydroxy-phenyl)-3(R),4-dimethyl-piperidin-1-yl]-propionyl}-amino)-3-phenyl-propionic acid (20a)

A solution dimethylformamide/piperidine 20:80 (100 mL) was added to the Fmoc-Phe Wang resin 1a (0.6 mmol/g, 3 g, 0.0018 mol) and the suspension was mixed at room temperature for 20 min. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of the resulting resin 2a in a mixture dichloromethane/tetrahydrofuran 1:3 (100 mL) was added consecutively 2,6-lutidine (0.84 mL, 0.0072 mol, 4 eq) and 2,4-dinitrobenzenesulfonyl chloride (1.92 g, 0.0072 mol, 4 eq). The mixture was shaken for 12 h at room temperature. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of the resulting resin 15a (0.200 g, 0.00012 mol, 1 eq) in tetrahydrofuran (20 mL) was added consecutively a 2M solution of triphenylphosphine in tetrahydrofuran (0.6 mL, 0.0012 mol, 10 eq), a 2M solution of diisopropylazodicarboxylate (DIAD) in tetrahydrofuran (0.6 mL, 0.0012 mol, 10 eq) and ethyl alcohol (0.055 g, 0.0012 mol, 10 eq). The mixture was shaken for 12 h at room temperature. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. A solution dimethylformamide/n-butylamine 80:20 (100 mL) was added to the resin 16a obtained previously and the suspension was mixed at room temperature for 6 hours (Scheme 4). The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of the resulting resin 17a in dichloromethane (20 mL) was added diisopropylethylamine (0.21 mL, 0.0012 mol, 10 eq) followed by acryloyl chloride (0.10 mL, 0.0012 mol, 10 eq). The mixture was shaken at room temperature for 6 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of the resulting resin 18a in MeOH/THF 1:2 (20 mL) was added a 0.18M solution of (+)-4(R)-(3-hydroxyphenyl)-3(R),4-dimethyl-1-piperidine (12) in MeOH/THF 1:2 (1 mL, 0.00018 mol, 1.5 eq) and the mixture was stirred at room temperature for 12 hours. The resin was then drained, washed consecutively with dimethylformamide (5×), dimethylformamide/water (9:1) (5×), dimethylformamide (5×), methanol (5×), dichloromethane (5×) and re-suspended in MeOH/THF 1:2 (20 mL). A 0.18M solution of (+)-4(R)-(3-hydroxyphenyl)-3(R),4-dimethyl-1-piperidine (12) in MeOH/THF 1:2 (1 mL, 0.00018 mol, 1.5 eq) was added to the mixture which was stirred at room temperature for an additional 12 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. The resin 19a was shaken in a mixture trifluoroacetic acid/dichloromethane (1:1) (10 mL) at room temperature for 20 minutes. The filtrate was collected and the resin was further washed with dichloromethane (3×2 mL). Evaporation of the filtrate afforded the desired compound further purified by routine HPLC. For Example 4 (20a), $R^8$=(S)$CH_2$Ph; $R^3$=H, $R^4$=$C_2H_5$; Mass spectral analysis: m/z=453 (M+H)$^+$.

Example 5

2(S)-(4-methoxyphenyl-{3-[4(R)-(3-Hydroxy-phenyl)-3(R),4-dimethylpiperidin-1-yl]-propionyl}-phenyl-amino)-3-phenyl-propionic acid (24a)

The resin 2a (0.00015 mol) was swelled in dry tetrahydrofuran (5 mL) and the following reagents were added in a sequential fashion: 4-methoxyphenylboronic acid (0.091 g, 0.0006 mol, 4 eq), anhydrous copper acetate (0.055 g, 0.0003 mol, 2 eq), 4 Å powdered molecular sieves (0.170 g) and triethylamine (0.083 mL, 0.0006 mol, 4 eq). The heterogeneous mixture was mixed for 16 h at room temperature. The resin was filtered and was washed alternately with tetrahydrofuran (7×) and dichloromethane (5×) followed by tetrahydrofuran (5×). To a suspension of the resin 21a obtained previously in dichloromethane (20 mL) was added diisopropylethylamine (0.26 mL, 0.0015 mol, 10 eq) followed by acryloyl chloride (0.12 mL, 0.0015 mol, 10 eq). The mixture was shaken at room temperature for 6 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. To a suspension of resin 22a obtained previously in MeOH/THF 1:2 (20 mL) was added a 0.18M solution of (+)-4(R)-(3-hydroxyphenyl)-3(R),4-dimethyl-1-piperidine (12) in MeOH/THF 1:2 (1 mL, 0.00018 mol, 1.5 eq) and the mixture was stirred at room temperature for 12 hours. The resin was then drained, washed consecutively with dimethylformamide (5×), dimethylformamide/water (9:1) (5×), dimethylformamide (5×), methanol (5×), dichloromethane (5×) and re-suspended in MeOH/THF 1:2 (20 mL). A 0.18M solution of (+)-4(R)-(3-hydroxyphenyl)-3(R),4-dimethyl-1-piperidine (12) in MeOH/THF 1:2 (1 mL, 0.00018 mol, 1.5 eq) was added to the mixture which was stirred at room temperature for an additional 12 hours. The resin was then drained, washed consecutively with dimethylformamide (5×), dimethylformamide/water (9:1) (5×), dimethylformamide (5×), methanol (5×), dichloromethane (5×), diethyl ether (5×) and dried under vacuum. The resin 23a was shaken in a mixture trifluoroacetic acid/dichloromethane (1:1) (10 mL) at room temperature for 20 min The filtrate was collected and the resin was further washed with dichloromethane (3×2 mL). Evaporation of the filtrate afforded the desired compound further purified by routine HPLC. For Example 5 (24a), $R^8$=(S)$CH_2$Ph; $R^4$=$CH_3OC_6H_4$(p); Mass spectral analysis: m/z=531 (M+H)$^+$.

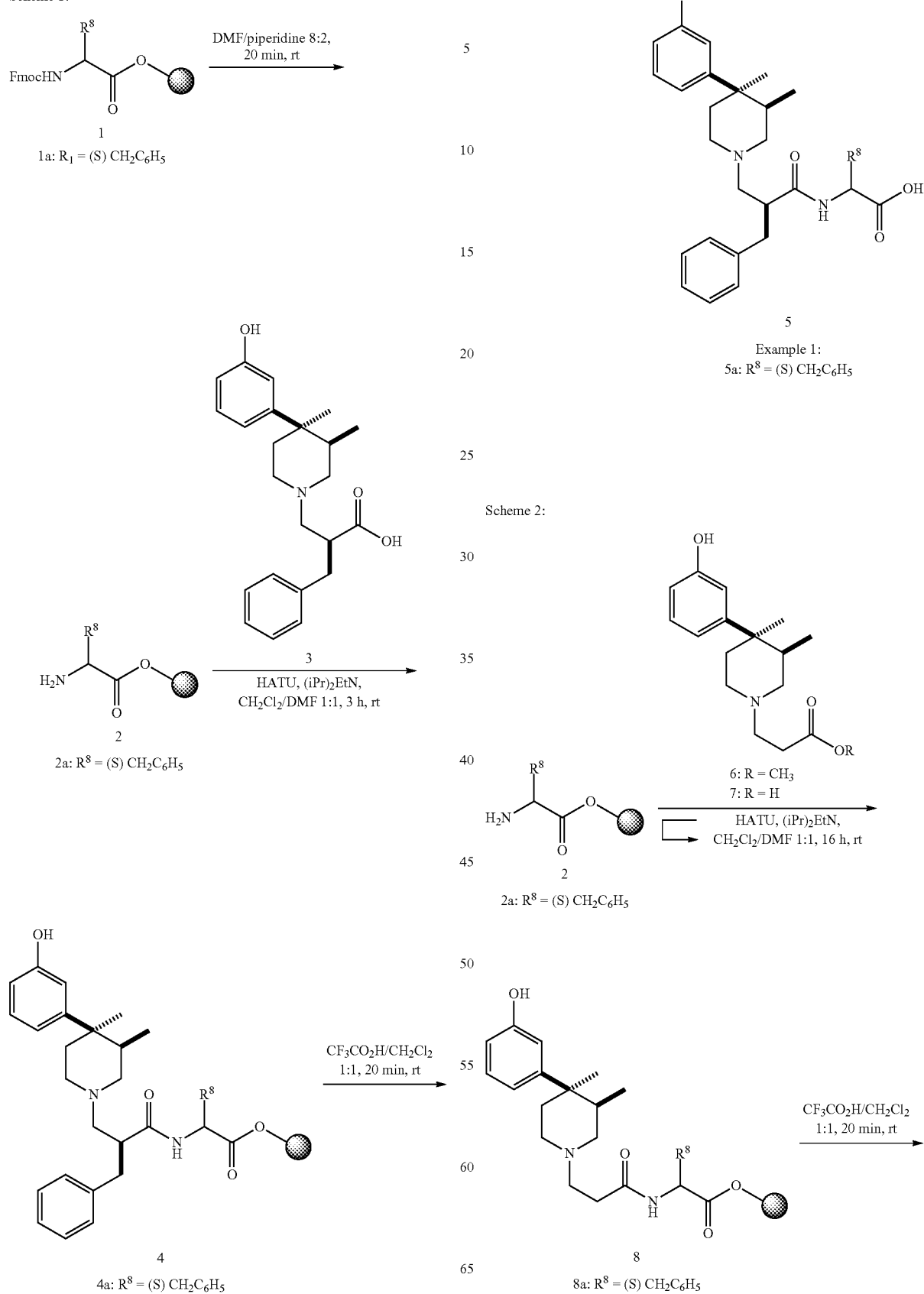

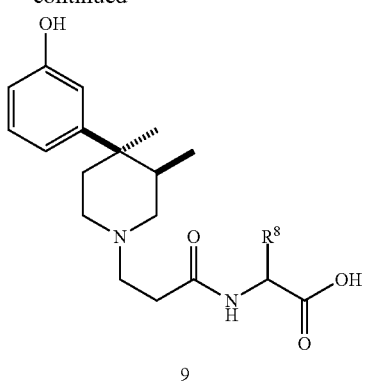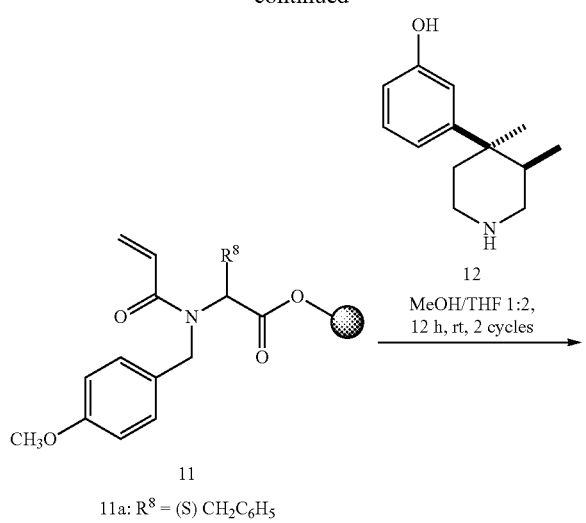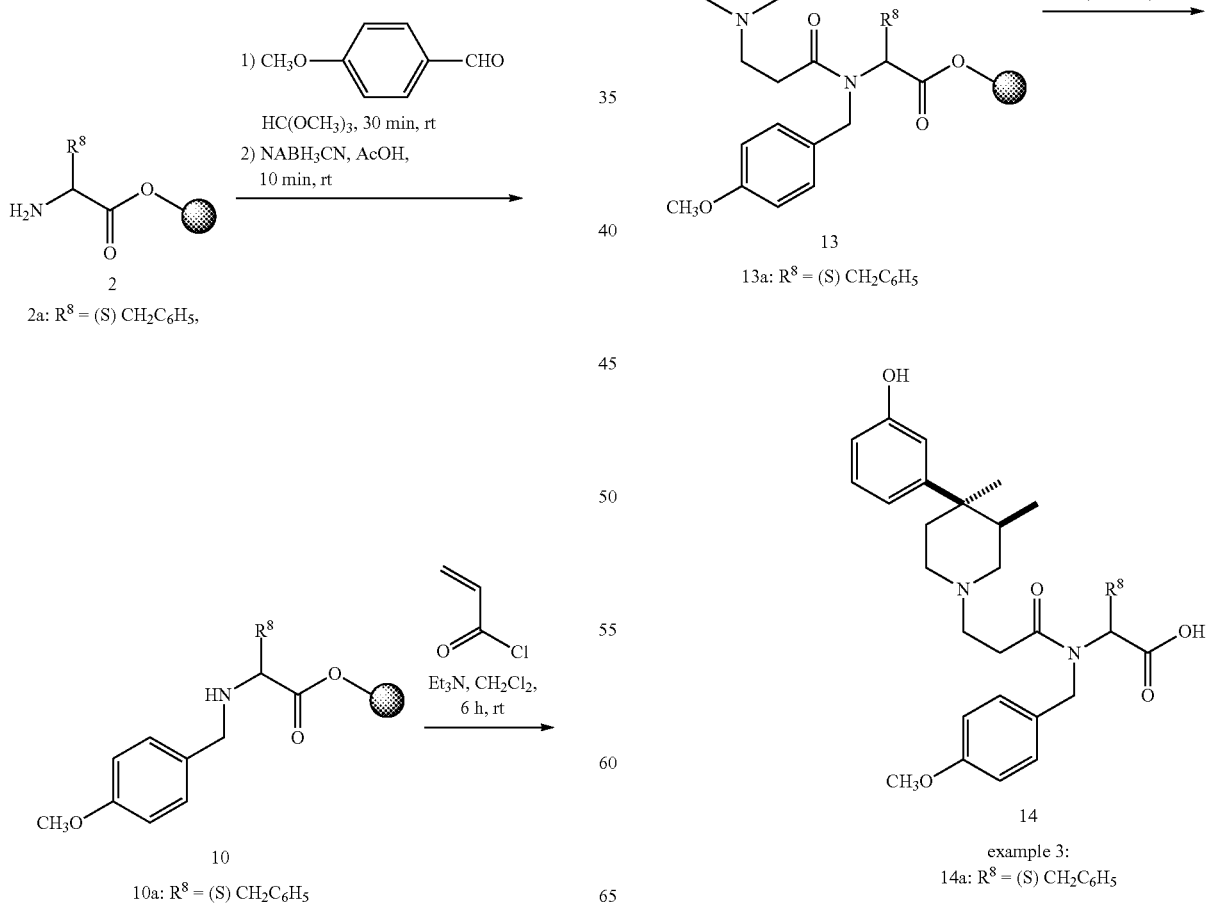

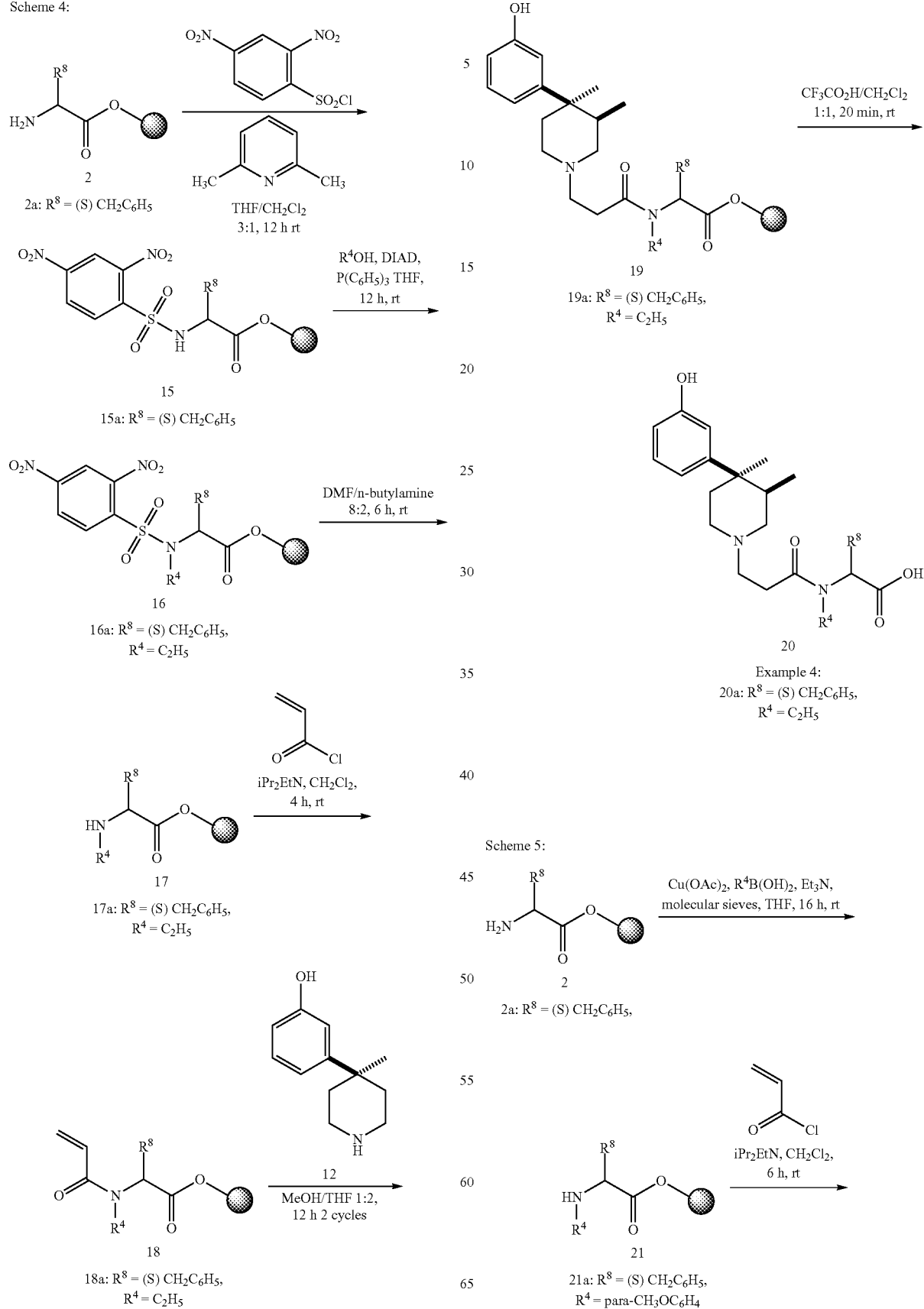

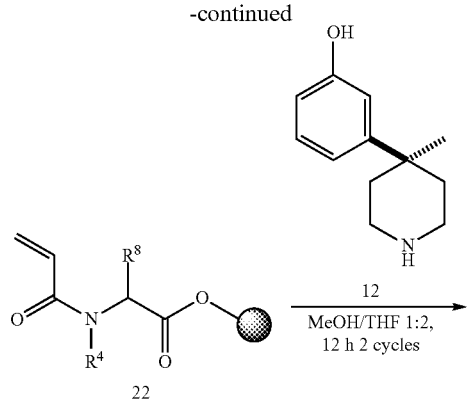

22a: $R^8$ = (S) $CH_2C_6H_5$,
$R^4$ = para-$CH_3OC_6H_4$

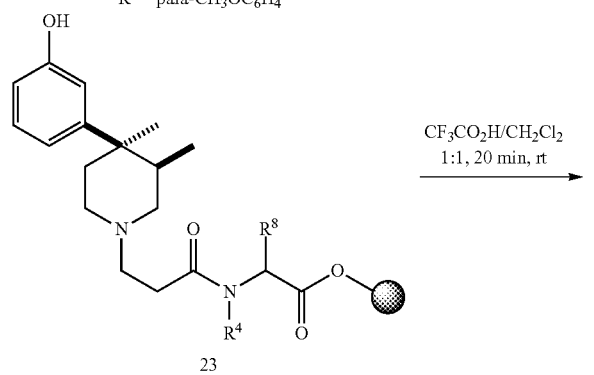

23a: $R^8$ = (S) $CH_2C_6H_5$,
$R^4$ = para-$CH_3OC_6H_4$

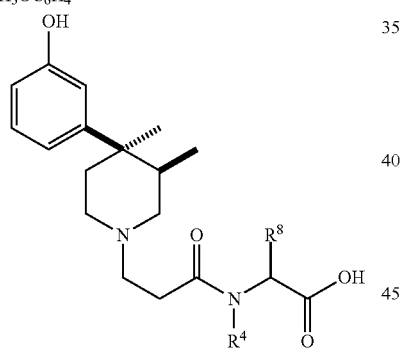

Example 5: 24a: $R^8$ = (S) $CH_2C_6H_5$,
$R^4$ = para-$CH_3OC_6H_4$

Biological Assays

The potencies of the compounds were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. $IC_{50}$ values were obtained by nonlinear analysis of the data using GraphPad Prism version 3.00 for Windows (GraphPad Software, San Diego). $K_i$ values were obtained by Cheng-Prusoff corrections of $IC_{50}$ values.

Receptor Binding (In Vitro Assay)

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and $LogEC_{50}$ is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[ligand]}{K_d}}$$

where [ligand] is the concentration of radioligand and $K_d$ is the equilibrium dissociation constant for the radioligand.

The potencies of the antagonists were assessed by their abilities to inhibit agonist-stimulated [$^{35}$S]GTPγS binding to membranes containing the cloned human μ, κ, or δ opioid receptors. The agonists used were loperamide for the μ opioid receptor, U50488H for the κ opioid receptor, and BW373U86 for the δ opioid receptor.

To determine the $IC_{50}$ value, which was the concentration to give half-maximal inhibition of agonist-stimulated [$^{35}$S]GTPγS binding, the amount of [$^{35}$S]GTPγS bound in the presence of a fixed concentration of agonist and various concentrations of antagonist was measured. The fixed concentration of agonist was the $EC_{80}$ for the agonist, which was the concentration to give 80% of the relative maximum stimulation of [$^{35}$S]GTPγS binding. The $IC_{50}$ value was determined from a best nonlinear regression fit of the data to the following equation, $$Y = \text{Bottom} + \frac{(\text{Top} - \text{Bottom})}{1 + 10^{X - LogIC50}}$$

where Y is the amount of [$^{35}$S]GTPγS bound at each concentration of antagonist, Bottom is the calculated amount of [$^{35}$S]GTPγS bound in the presence of an infinite concentration of antagonist, Top is the calculated amount of [$^{35}$S] GTPγS bound in the absence of added antagonist, X is the logarithm of the concentration of antagonist, and LogIC$_{50}$ is the logarithm of the concentration of antagonist where the amount of [$^{35}$S]GTPγS bound is halfway between Bottom and Top. The nonlinear regression fit was performed using GraphPad Prism® version 3.00 for Windows (GraphPad Software, San Diego, Calif.).

The compounds described in Table 1 (Examples 1 to 82) were tested for their affinity towards the μ, δ and κ opioid receptors. All of these compounds bind with affinity less than 100 μM to the μ, δ and κ opioid receptors. These compounds displayed various degree of selectivity μ v, δ, μ v, κ and κ v, δ. The activity of selected ligands was also evaluated in vitro. Numerous compounds were found to be pure antagonist at the μ opioid receptor (no agonist activity detectable at concentration >10 μM). As examples, compound 28 (Table 1) binds to the μ, δ and κ opioid receptors with affinity (expressed as K$_i$ value) of 0.4 nM, 510 nM and 200 nM, respectively. Furthermore, the compound 28 displayed potent in vitro antagonist activity (IC$_{50}$=1.4 nM). The compound 30 binds to the μ, δ and κ opioid receptors with affinity (expressed as K$_i$ value) of 0.4 nM, 860 nM and 440 nM, respectively. Furthermore, the compound 30 displayed potent in vitro antagonist activity (IC$_{50}$=1.0 nM).

Mouse Gastrointestinal Transit (GIT) Assay (In Vivo Assay)

The antagonist activity of compounds may be evaluated using the Mouse Gastrointestinal Transit (GIT) Assay (in vivo assay). Male Swiss-Webster mice (typically 25-30 g) are used for all experiments. Mice are housed 4/cage in polycarbonate cages with food and water available ad libitum. Mice are on a 12 hours light:dark schedule with lights on at 6:30 a.m. All experiments are performed during the light cycle. Mice are fasted the night before the experiment, with water available ad libitum.

Mice are administered vehicle (10% DMSO:20% Cremophor EL:70% saline) or test compound (10 mg/kg) orally 2 or 6 hours before determination of GIT. Compounds are administered in a volume of 0.1 ml/10 g of body weight. Morphine (3 mg/kg) or vehicle (0.9% saline) is administered s.c. 35 minutes prior to determination of GIT. Ten minutes after the morphine treatment, mice are administered 0.2 ml of a charcoal meal orally. The charcoal meal consists of a slurry of charcoal, flour, and water in the following ratio (1:2:8, w:w:v). Twenty-five minutes after receiving the charcoal meal, the mice are euthanized with CO$_2$ and GIT determined GIT is expressed as the % GIT by the following formula:

$$\frac{(\text{distance to leading edge of charcoal meal (cm)})}{(\text{total length of the small intestine (cm)})} \times 100.$$

For each compound a % Antagonism (% A) value is determined for the 2 and 6-hour antagonist pretreatment. Using the mean % GIT for each treatment group, % A is calculated using the following formula:

$$1 - \left( \frac{\begin{pmatrix} \text{mean vehicle response} - \text{mean antagonist} + \\ \text{morphine response} \end{pmatrix}}{(\text{mean vehicle response} - \text{mean morphine response})} \right) \times 100$$

TABLE 1

| Example | Name | [M + H]$^+$ |
|---|---|---|
| 1 | 2(S)-{2(S)-Benzyl-3-[4(R)-(3-hydroxy-phenyl)-3(R),4-dimethyl-piperidin-1-yl]-propionylamino}-3-phenyl-propionic acid | 515 |
| 2 | 2(S)-{3-[4(R)-(3-Hydroxy-phenyl)-3(R),4-dimethyl-piperidin-1-yl]-propionylamino}-3-phenyl-propionic acid | 425 |
| 3 | 2(S)-[{3-[4(R)-(3-Hydroxy-phenyl)-3(R),4-dimethyl-piperidin-1-yl]-propionyl}-(4-methoxy-benzyl)-amino]-3-phenyl-propionic acid | 545 |
| 4 | 2(S)-(Ethyl-{3-[4(R)-(3-hydroxy-phenyl)-3(R),4-dimethyl-piperidin-1-yl]-propionyl}-amino)-3-phenyl-propionic acid | 453 |
| 5 | 2(S)-({3-[4(R)-(3-Hydroxy-phenyl)-3(R),4-dimethyl-piperidin-1-yl]-propionyl}-phenyl-amino)-3-(4-methoxyphenyl)-propionic acid | 531 |
| 6 | 2(S)-{2(S)-Benzyl-3-[4(R)-(3-hydroxy-phenyl)-3(R),4-dimethyl-piperidin-1-yl]-propionylamino}-propionic acid | 439 |
| 7 | 1-{2(S)-Benzyl-3-[4(R)-(3-hydroxy-phenyl)-3(R),4-dimethyl-piperidin-1-yl]-propionyl}-pyrrolidine-2(R)-carboxylic acid | 465 |
| 8 | 6-{2(S)-Benzyl-3-[4(R)-(3-hydroxy-phenyl)-3(R),4-dimethyl-piperidin-1-yl]-propionylamino}-hexanoic acid | 481 |
| 9 | 2(S)-{2(S)-Benzyl-3-[4(R)-(3-hydroxy-phenyl)-3(R),4-dimethyl-piperidin-1-yl]-propionylamino}-3-cyclohexyl-propionic acid | 521 |
| 10 | {2(S)-Benzyl-3-[4(R)-(3-hydroxy-phenyl)-3(R),4-dimethyl-piperidin-1-yl]-propionylamino}-(S)-cyclohexyl-acetic acid | 507 |
| 11 | 2(S)-{2(S)-Benzyl-3-[4(R)-(3-hydroxy-phenyl)-3(R),4-dimethyl-piperidin-1-yl]-propionylamino}-4-phenyl-butyric acid | 529 |
| 12 | 2(R)-{2(S)-Benzyl-3-[4(R)-(3-hydroxy-phenyl)-3(R),4-dimethyl-piperidin-1-yl]-propionylamino}-3-(4-fluoro-phenyl)-propionic acid | 533 |
| 13 | 2(S)-{2(S)-Benzyl-3-[4(R)-(3-hydroxy-phenyl)-3(R),4-dimethyl-piperidin-1-yl]-propionylamino}-3-(4-nitro-phenyl)-propionic acid | 560 |
| 14 | {2(S)-Benzyl-3-[4(R)-(3-hydroxy-phenyl)-3(R),4-dimethyl-piperidin-1-yl]-propionylamino}-(R)-phenyl-acetic acid | 501 |
| 15 | {2(S)-Benzyl-3-[4(R)-(3-hydroxy-phenyl)-3(R),4-dimethyl-piperidin-1-yl]-propionylamino}-(S)-phenyl-acetic acid | 501 |
| 16 | 2-{2(S)-Benzyl-3-[4(R)-(3-hydroxy-phenyl)-3(R),4-dimethyl-piperidin-1-yl]-propionyl}-1,2,3,4-tetrahydro-isoquinoline-3(S)-carboxylic acid | 527 |
| 17 | 2(S)-{2(S)-Benzyl-3-[4(R)-(3-hydroxy-phenyl)-3(R),4-dimethyl-piperidin-1-yl]-propionylamino}-3-biphenyl-4-yl-propionic acid | 591 |
| 18 | 2(S)-{2(S)-Benzyl-3-[4(R)-(3-hydroxy-phenyl)-3(R),4-dimethyl-piperidin-1-yl]-propionylamino}-4-methylsulfanyl-butyric acid | 499 |
| 19 | 2(S)-{2(S)-Benzyl-3-[4(R)-(3-hydroxy-phenyl)-3(R),4-dimethyl-piperidin-1-yl]-propionylamino}-3-naphthalen-1-yl-propionic acid | 565 |
| 20 | 2(R)-{2(S)-Benzyl-3-[4(R)-(3-hydroxy-phenyl)-3(R),4-dimethyl-piperidin-1-yl]-propionylamino}-3-naphthalen-1-yl-propionic acid | 566 |
| 21 | 2(S)-{2(S)-Benzyl-3-[4(R)-(3-hydroxy-phenyl)-3(R),4-dimethyl-piperidin-1-yl]-propionylamino}-3-naphthalen-2-yl-propionic acid | 565 |
| 22 | 2(S)-{2(S)-Benzyl-3-[4(R)-(3-hydroxy-phenyl)-3(R),4-dimethyl-piperidin-1-yl]-propionylamino}-3-(4-iodo-phenyl)-propionic acid | 641 |

TABLE 1-continued

| Example | Name | [M + H]+ |
|---|---|---|
| 23 | 1-{2(S)-Benzyl-3-[4(R)-(3-hydroxy-phenyl)-3(R),4-dimethyl-piperidin-1-yl]-propionyl}-pyrrolidine-2-(S)-carboxylic acid | 465 |
| 24 | 3-(Acetylamino-methylsulfanyl)-2-(S)-{2(S)-benzyl-3-[4(R)-(3-hydroxy-phenyl)-3(R),4-dimethyl-piperidin-1-yl]-propionylamino}-propionic acid | 542 |
| 25 | 3-(4-Benzoyl-phenyl)-2-(S)-{2(S)-benzyl-3-[4(R)-(3-hydroxy-phenyl)-3(R),4-dimethyl-piperidin-1-yl]-propionylamino}-propionic acid | 619 |
| 26 | 2(R)-{2(S)-Benzyl-3-[4(R)-(3-hydroxy-phenyl)-3(R),4-dimethyl-piperidin-1-yl]-propionylamino}-propionic acid | 439 |
| 27 | 2(S)-{2(S)-Benzyl-3-[4(R)-(3-hydroxy-phenyl)-3(R),4-dimethyl-piperidin-1-yl]-propionylamino}-succinic acid | 483 |
| 28 | 5-Amino-2(S)-{2(S)-benzyl-3-[4(R)-(3-hydroxy-phenyl)-3(R),4-dimethyl-piperidin-1-yl]-propionylamino}-pentanoic acid | 482 |
| 29 | 2(S)-{2(S)-Benzyl-3-[4(R)-(3-hydroxy-phenyl)-3(R),4-dimethyl-piperidin-1-yl]-propionylamino}-3-hydroxy-propionic acid | 455 |
| 30 | 6-Amino-2(S)-{2(S)-benzyl-3-[4(R)-(3-hydroxy-phenyl)-3(R),4-dimethyl-piperidin-1-yl]-propionylamino}-hexanoic acid | 496 |
| 31 | 3-Amino-2(S)-{2(S)-benzyl-3-[4(R)-(3-hydroxy-phenyl)-3(R),4-dimethyl-piperidin-1-yl]-propionylamino}-propionic acid | 454 |
| 32 | 2(S)-{2(S)-Benzyl-3-[4(R)-(3-hydroxy-phenyl)-3(R),4-dimethyl-piperidin-1-yl]-propionylamino}-pentanedioic acid | 497 |
| 33 | 2(S)-{2(S)-Benzyl-3-[4(R)-(3-hydroxy-phenyl)-3(R),4-dimethyl-piperidin-1-yl]-propionylamino}-3-(1H-indol-3-yl)-propionic acid | 554 |
| 34 | 1-{2(S)-Benzyl-3-[4(R)-(3-hydroxy-phenyl)-3(R),4-dimethyl-piperidin-1-yl]-propionyl}-4(R)-hydroxy-pyrrolidine-2(S)-carboxylic acid | 481 |
| 35 | 2(S)-{2(S)-Benzyl-3-[4(R)-(3-hydroxy-phenyl)-3(R),4-dimethyl-piperidin-1-yl]-propionylamino}-3-(4-hydroxy-phenyl)-propionic acid | 531 |
| 36 | 2(S)-{2(S)-Benzyl-3-[4(R)-(3-hydroxy-phenyl)-3(R),4-dimethyl-piperidin-1-yl]-propionylamino}-3-(1H-imidazol-4-yl)-propionic acid | 505 |
| 37 | 2-{3-[4(R)-(3-Hydroxy-phenyl)-3(R),4-dimethyl-piperidin-1-yl]-propionyl}-1,2,3,4-tetrahydro-isoquinoline-3(S)-carboxylic acid | 437 |
| 38 | 3-(4-Fluoro-phenyl)-2(S)-{3-[4(R)-(3-hydroxy-phenyl)-3(R),4-dimethyl-piperidin-1-yl]propionylamino}-propionic acid | 443 |
| 39 | 3-Cyclohexyl-2(S)-{3-[4(R)-(3-hydroxy-phenyl)-3(R),4-dimethyl-piperidin-1-yl]-propionylamino}-propionic acid | 431 |
| 40 | (S)-Cyclohexyl-{3-[4(R)-(3-hydroxy-phenyl)-3(R),4-dimethyl-piperidin-1-yl]-propionylamino}-acetic acid | 417 |
| 41 | 2(S)-{3-[4(R)-(3-Hydroxy-phenyl)-3(R),4-dimethyl-piperidin-1-yl]-propionylamino}-4-phenyl-butyric acid | 439 |
| 42 | 2(S)-{3-[4(R)-(3-Hydroxy-phenyl)-3(R),4-dimethyl-piperidin-1-yl]-propionylamino}-3-(4-nitro-phenyl)-propionic acid | 470 |
| 43 | 2(S)-{3-[4(R)-(3-Hydroxy-phenyl)-3(R),4-dimethyl-piperidin-1-yl]-propionylamino}-3-naphthalen-1-yl-propionic acid | 475 |
| 44 | 2(S)-{3-[4(R)-(3-Hydroxy-phenyl)-3(R),4-dimethyl-piperidin-1-yl]-propionylamino}-3-(4-iodo-phenyl)-propionic acid | 551 |
| 45 | 3-(4-Benzoyl-phenyl)-2(S)-{3-[4(R)-(3-hydroxy-phenyl)-3(R),4-dimethyl-piperidin-1-yl]-propionylamino}-propionic acid | 529 |
| 46 | 6-{3-[4(R)-(3-Hydroxy-phenyl)-3(R),4-dimethyl-piperidin-1-yl]-propionylamino}-hexanoic acid | 391 |
| 47 | 2(S)-{3-[4(R)-(3-Hydroxy-phenyl)-3(R),4-dimethyl-piperidin-1-yl]-propionylamino}-4-methylsulfanyl-butyric acid | 409 |
| 48 | 2(R)-{3-[4(R)-(3-Hydroxy-phenyl)-3(R),4-dimethyl-piperidin-1-yl]-propionylamino}-3-naphthalen-1-yl-propionic acid | 475 |
| 49 | 2(S)-{3-[4(R)-(3-Hydroxy-phenyl)-3(R),4-dimethyl-piperidin-1-yl]-propionylamino}-3-naphthalen-2-yl-propionic acid | 475 |
| 50 | {3-[4(R)-(3-Hydroxy-phenyl)-3(R),4-dimethyl-piperidin-1-yl]-propionylamino}-(S)-phenyl-acetic acid | 411 |
| 51 | 2(S)-{3-[4(R)-(3-Hydroxy-phenyl)-3(R),4-dimethyl-piperidin-1-yl]-propionylamino}-succinic acid | 393 |
| 52 | 2(S)-{3-[4(R)-(3-Hydroxy-phenyl)-3(R),4-dimethyl-piperidin-1-yl]-propionylamino}-pentanedioic acid | 407 |
| 53 | 5-Amino-2(S)-{3-[4(R)-(3-hydroxy-phenyl)-3(R),4-dimethyl-piperidin-1-yl]-propionylamino}-pentanoic acid | 392 |
| 54 | 6-Amino-2(S)-{3-[4(R)-(3-hydroxy-phenyl)-3(R),4-dimethyl-piperidin-1-yl]-propionylamino}-hexanoic acid | 406 |
| 55 | 3-Amino-2(S)-{3-[4(R)-(3-hydroxy-phenyl)-3(R),4-dimethyl-piperidin-1-yl]-propionylamino}-propionic acid | 364 |
| 56 | 2(S)-{3-[4(R)-(3-Hydroxy-phenyl)-3(R),4-dimethyl-piperidin-1-yl]-propionylamino}-succinamic acid | 392 |
| 57 | 2(S)-{3-[4(R)-(3-Hydroxy-phenyl)-3(R),4-dimethyl-piperidin-1-yl]-propionylamino}-3-(1H-indol-3-yl)-propionic acid | 464 |
| 58 | 4(R)-Hydroxy-1-{3-[4(R)-(3-hydroxy-phenyl)-3(R),4-dimethyl-piperidin-1-yl]-propionyl}-pyrrolidine-2(R)-carboxylic acid | 391 |
| 59 | 3-(4-Hydroxy-phenyl)-2(S)-{3-[4(R)-(3-hydroxy-phenyl)-3(R),4-dimethyl-piperidin-1-yl]-propionylamino}-propionic acid | 441 |
| 60 | 2(S)-{3-[4(R)-(3-Hydroxy-phenyl)-3(R),4-dimethyl-piperidin-1-yl]-propionylamino}-3-(1H-imidazol-4-yl)-propionic acid | 415 |
| 61 | 1-{3-[4-(3-Hydroxy-phenyl)-3,4-dimethyl-piperidin-1-yl]-propionyl}-pyrrolidine-2(R)-carboxylic acid | 375 |
| 62 | 3-(Acetylamino-methylsulfanyl)-2(S)-{3-[4(R)-(3-hydroxy-phenyl)-3(R),4-dimethyl-piperidin-1-yl]-propionylamino}-propionic acid | 452 |
| 63 | 3-Hydroxy-2(S)-{3-[4(R)-(3-hydroxy-phenyl)-3(R),4-dimethyl-piperidin-1-yl]-propionylamino}-propionic acid | 365 |
| 64 | 4-Carbamoyl-2(S)-{3-[4(R)-(3-hydroxy-phenyl)-3(R),4-dimethyl-piperidin-1-yl]-propionylamino}-butyric acid | 406 |
| 65 | 2(R)-{3-[4(R)-(3-Hydroxy-phenyl)-3(R),4-dimethyl-piperidin-1-yl]-propionylamino}-propionic acid | 349 |
| 66 | 3-Biphenyl-4-yl-2(S)-{3-[4(R)-(3-Hydroxy-phenyl)-3(R),4-dimethyl-piperidin-1-yl]-propionylamino}-propionic acid | 501 |
| 67 | 2(S)-((3-Benzyloxy-benzyl)-{3-[4(R)-(3-hydroxy-phenyl)-3(R),4-dimethyl-piperidin-1-yl]-propionyl}-amino)-3-phenyl-propionic acid | 621 |
| 68 | 2(S)-(Biphenyl-4-ylmethyl-{3-[4(R)-(3-hydroxy-phenyl)-3(R),4-dimethyl-piperidin-1-yl]-propionyl}-amino)-3-phenyl-propionic acid | 591 |
| 69 | 2(S)-((3-Chloro-benzyl)-{3-[4(R)-(3-hydroxy-phenyl)-3(R),4-dimethyl-piperidin-1-yl]-propionyl}-amino)-3-phenyl-propionic acid | 549 |
| 70 | 2(S)-[{3-[4(R)-(3-Hydroxy-phenyl)-3(R),4-dimethyl-piperidin-1-yl]-propionyl}-(3-phenoxy-benzyl)-amino]-3-phenyl-propionic acid | 607 |
| 71 | 2(S)-({3-[4(R)-(3-Hydroxy-phenyl)-3(R),4-dimethyl-piperidin-1-yl]-propionyl}-methyl-amino)-3-phenyl-propionic acid | 439 |
| 72 | 2(S)-({3-[4(R)-(3-Hydroxy-phenyl)-3(R),4-dimethyl-piperidin-1-yl]-propionyl}-isobutyl-amino)-3-phenyl-propionic acid | 481 |
| 73 | 2(S)-(Cyclopropylmethyl-{3-[4(R)-(3-hydroxy-phenyl)-3(R),4-dimethylpiperidin-1-yl]-propionyl}-amino)-3-phenyl-propionic acid | 479 |
| 74 | 2(S)-(Hex-3-enyl-{3-[4(R)-(3-hydroxy-phenyl)-3(R),4-dimethylpiperidin-1-yl]-propionyl}-amino)-3-phenyl-propionic acid | 507 |
| 75 | 2(S)-({3-[4(R)-(3-Hydroxy-phenyl)-3(R),4-dimethyl-piperidin-1-yl]-propionyl}-phenethyl-amino)-3-phenyl-propionic acid | 529 |

TABLE 1-continued

| Example | Name | [M + H]+ |
|---|---|---|
| 76 | 2(S)-(Benzyl-{3-[4(R)-(3-hydroxy-phenyl)-3(R),4-dimethyl-piperidin-1-yl]-propionyl}-amino)-3-phenyl-propionic acid | 515 |
| 77 | 2(S)-[{3-[4(R)-(3-Hydroxy-phenyl)-3(R),4-dimethyl-piperidin-1-yl]-propionyl}-(2-morpholin-4-yl-ethyl)-amino]-3-phenyl-propionic acid | 538 |
| 78 | 2(S)-((2-Amino-ethyl)-{3-[4(R)-(3-hydroxy-phenyl)-3(R),4-dimethyl-piperidin-1-yl]-propionyl}-amino)-3-phenyl-propionic acid | 468 |
| 79 | 2(S)-({3-[4(R)-(3-Hydroxy-phenyl)-3(R),4-dimethyl-piperidin-1-yl]-propionyl}-phenyl-amino)-3-phenyl-propionic acid | 501 |
| 80 | 2(S)-[{3-[4(R)-(3-Hydroxy-phenyl)-3(R),4-dimethyl-piperidin-1-yl]-propionyl}-(3-phenoxy-benzyl)-amino]-3-(4-methoxycarbonylphenyl)-propionic acid | 559 |
| 81 | 2S-Benzyl-3-[4-(3-hydroxy-phenyl)-3R,4R-dimethyl-piperidin-1-yl]-N-trifluoromethylsulfonyl-propionamide | 499 |
| 82 | ({2S-Benzyl-3-[4-(3-hydroxy-phenyl)-3R,4R-dimethyl-piperidin-1-yl]-propionylamino}-methyl)-phosphonic acid | 461 |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

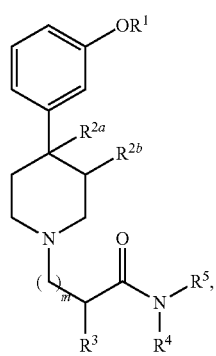

wherein:
R$^1$ is H or alkyl;
R$^{2a}$ is alkyl;
R$^{2b}$ is H, or alkyl;
R$^3$ is H, alkyl,-or aralkyl;
R$^4$ is
H, or
alkyl
R$^5$ is —CH$_2$P(=O)OR$^{7b}$OR$^{7c}$;
R$^{7b}$, and R$^{7c}$ are each independently H, or alkyl m is the integer 0, 1, 2, 3, or 4;

or a pharmaceutically acceptable salt thereof.

2. A compound according to claim 1, wherein R$^1$ is H.

3. A compound according to claim 1, wherein R$^{2a}$ and R$^{2b}$ are trans to each other.

4. A compound according to claim 1, of formula II:

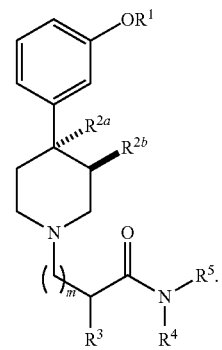

5. A compound according to claim 1, wherein R$^{2a}$ and R$^{2b}$ are each methyl.

6. A compound according to claim 1, of formula III:

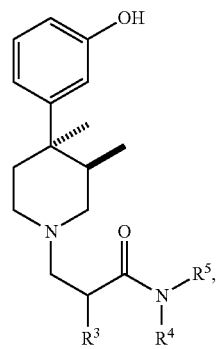

wherein:
R$^3$ is aralkyl.

7. A compound according to claim 1, wherein R$^3$ is:

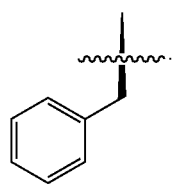

8. A compound according to claim 7, wherein R$^1$ is H, R$^{2a}$ and R$^{2b}$ are each methyl and are trans to each other, m is the integer 1, R$^4$ is H, and R$^{7b}$, and R$^{7c}$ are each independently H or methyl.

9. A compound according to claim 5, wherein $R^3$ is:

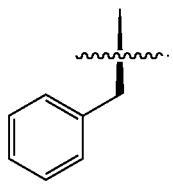

10. A compound according to claim 4, wherein $R^{2a}$ and $R^{2b}$ are each methyl.

11. A compound according to claim 1, of formula IX:

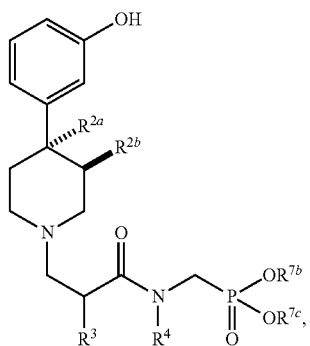

wherein:

$R^3$ is H, alkyl, or aralkyl.

12. A compound according to claim 1, wherein $R^4$ is H.

13. A compound according to claim 1, wherein m is the integer 1.

14. A pharmaceutical composition, comprising:

a pharmaceutically acceptable carrier; and an effective amount of a compound according to claim 1.

15. A pharmaceutical composition according to claim 14, further comprising an effective amount of at least one opioid.

16. A pharmaceutical composition according to claim 15, wherein said opioid is alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

17. A pharmaceutical composition comprising the compound ({2S-Benzyl -3-[4-(3-hydroxyphenyl)-3R,4R-dimethylpiperidin-l-yl]-propionylamino }-methyl)-phosphonic acid or a pharmaceutically acceptable salt thereof.

* * * * *